(12) United States Patent
Rizzone

(10) Patent No.: US 9,662,411 B2
(45) Date of Patent: May 30, 2017

(54) MOBILE ULTRAVIOLET STERILIZATION SYSTEMS AND METHODS

(71) Applicant: Alan Rizzone, Huntington Beach, CA (US)

(72) Inventor: Alan Rizzone, Huntington Beach, CA (US)

( * ) Notice: Subject to any disclaimer, the term of this patent is extended or adjusted under 35 U.S.C. 154(b) by 0 days.

(21) Appl. No.: 14/852,343

(22) Filed: Sep. 11, 2015

(65) Prior Publication Data

US 2016/0074546 A1     Mar. 17, 2016

Related U.S. Application Data

(60) Provisional application No. 62/049,903, filed on Sep. 12, 2014.

(51) Int. Cl.
*A61L 2/10* (2006.01)

(52) U.S. Cl.
CPC ............. *A61L 2/10* (2013.01); *A61L 2202/16* (2013.01); *A61L 2202/25* (2013.01)

(58) Field of Classification Search
CPC ........ A61L 2/00; A61L 2/0029; A61L 2/0047; A61L 2/08; A61L 2/10
USPC ... 250/453.11, 454.11, 455.11, 493.1, 494.1, 250/504 R, 504 H; 422/22, 24
See application file for complete search history.

(56) References Cited

U.S. PATENT DOCUMENTS

| | | | |
|---|---|---|---|
| 2,253,250 A * | 8/1941 | Selig | A61L 2/10 |
| | | | 250/455.11 |
| 2011/0215261 A1 * | 9/2011 | Lyslo | A61L 2/10 |
| | | | 250/492.1 |

* cited by examiner

*Primary Examiner* — Nicole Ippolito
(74) *Attorney, Agent, or Firm* — Rutan & Tucker, LLP

(57) ABSTRACT

Sterilization units and systems and related assemblies, devices, and methods are disclosed. The sterilization units may be mobile and used in a variety of locations. The sterilization units and systems use germicidal ultraviolet-C light to kill or render non-viable bacteria and viruses. The various sterilization units and systems disclosed herein may have improved ultraviolet light distribution and/or improved ability to direct and focus the ultraviolet light in a desired area. The sterilization units and systems may optionally be made of non-magnetic materials such that the sterilization units and systems may be used in the vicinity of MRI equipment without causing complications or damage to the MRI equipment.

26 Claims, 15 Drawing Sheets

MOBILE ULTRAVIOLET STERILIZATION SYSTEMS AND METHODS

CROSS-REFERENCE TO RELATED APPLICATIONS

This application claims the benefit of priority to U.S. Provisional Application No. 62/049,903, filed Sep. 12, 2014, which is incorporated by reference in its entirety into this application.

BACKGROUND

Sterilization is an ongoing concern in hospitals, medical offices, businesses, homes, restaurants, vehicles (e.g., food transportation vehicles), and other areas. Many diseases and infections are unnecessarily spread from host to host as people or animals come into contact with unsterilized items. Effective and efficient sterilization systems, devices, and methods can have a significant impact in preventing the spread of infections and disease.

Improved awareness and efforts to sterilize in hospitals and medical offices has helped prevent the spread of certain diseases and infections; however, otherwise preventable infections and diseases are still spread in hospitals around the world every day. For example, the United States Center for Disease Control has estimated that there were approximately 722,000 hospital-associated infections in United States acute care hospitals in 2011. The Center for Disease Control also estimates that about 75,000 hospital patients with hospital-associated infections died during their hospitalizations in 2011. Dealing with infections contracted in hospitals, including the associated care and potential liability issues, is a significant burden and cost to hospitals and medical practitioners. There is an ongoing need to find better ways to sterilize equipment, furniture, etc. in hospitals and other places to prevent the spread of disease and infections.

One challenge faced in hospitals is the difficulty of sterilizing large equipment, e.g., hospital gurneys, beds, wheelchairs, medical carts, waiting room furniture, tables, chairs, other furniture, etc. Often these larger items must be cleaned and disinfected by hand using cleaners, but this is not always effectively or timely done. There is a need for improved methods of sterilization of larger equipment that is easier and more effective.

Another challenge is that while some sterilization techniques and cleaners are effective at killing certain microorganism, e.g., certain bacteria, the sterilization techniques may not be effective at killing other microorganisms, e.g., viruses. There is a need for a sterilization technique that effectively and efficiently kills or renders non-viable all potentially harmful microorganisms or pathogens, including viruses.

Also, there is a rising concern in the medical community concerning treatment and sterilization techniques that lead to drug or antibiotic-resistant bacteria or microorganisms. Accordingly, the use of antibacterial soap, for example, is falling out of favor among many people due to fears that it is contributing to the increase in antibiotic-resistant bacteria. A sterilization device and technique that effectively kills or renders non-viable all the microorganisms or pathogens in a treatment area can help prevent the formation of antibacterial-resistant microorganisms. Further, an effective sterilization device and technique desirably will kill or render non-viable even antibacterial-resistant microorganisms, thereby preventing infection of a host by an antibacterial-resistant microorganism that might be more difficult to kill if allowed to infect a host.

Ultraviolet-A ("UV-A"), ultraviolet-B ("UV-B"), and ultraviolet-C ("UV-C") are part of the ultraviolet spectrum and most people are exposed to some of each type of UV light every day. UV-A is also known as "blacklight" and is generally harmless. UV-B has a high penetrating ability and prolonged exposure can result in skin cancer, skin aging, and cataracts. UV-C, also known as Germicidal irradiation, Germicidal UV or UVGI has strong penetrating ability and effectively kills or renders non-viable microorganisms including bacteria and viruses. UV-C light can be harmful to humans, but is often absorbed by the outer, dead layer of skin where harm may be limited.

UV-C light is desirable to use as a means of sterilizing various items/objects (e.g., equipment, instruments, furniture, rooms, etc.) because it is so effective at killing microorganisms, including bacteria and viruses. UV-C light is also desirable because it does not involve the use of toxic chemicals that might cause their own harm if used. UV-C light is simple and cost effective to use without causing pollution or requiring the use of toxic chemicals. Accordingly, UV-C sterilization units can be very effective for sterilization while minimizing harm to the environment or humans. Generally, when the terms "UV" or "ultraviolet" are used herein (unless further specified), these terms refer to germicidal UV-C light.

Various ultraviolet sterilization systems, devices/apparatuses, methods, etc. that provide for more effective sterilization in an easier and more-cost effective manner to address the needs and issues discussed above and other needs are described herein.

SUMMARY

Disclosed herein are novel apparatuses, systems, methods, etc. for sterilization using ultraviolet light.

In one embodiment, a sterilization chamber comprises walls enclosing a sterilization area, and one or more ultraviolet light bulbs attached to one or more of the walls inside the sterilization area, wherein the one or more ultraviolet light bulbs are capable of irradiating germicidal ultraviolet light at sufficient levels to kill or render non-viable microorganisms exposed to the ultraviolet light. The one or more ultraviolet light bulbs may be attached to the one or more of the walls through light fixtures mounted directly to the one or more of the walls. The sterilization chamber may also include a corrugated reflective material that lines an inside surface of the walls, and/or a control unit including controls to operate the one or more ultraviolet light bulbs. The lining of corrugated reflective material may be configured to reflect the UV light in the chamber in many different directions to help spread the light on every surface of an object being sterilized in the sterilization area. The lining of corrugated reflective material may be configured to reflect the UV light in the chamber in such a way that the object being sterilized in the sterilization area can be 100% sterilized or nearly 100% sterilized during a single sterilization procedure.

The walls of the sterilization chamber may be built onto a sturdy frame. One of the walls may be a door that can open or close to allow an object to be sterilized to enter the sterilization area, and a side of the door facing the interior of the sterilization chamber when the door is closed may include one or more than one of the one or more ultraviolet light bulbs attached to the side of the door facing the interior of the sterilization chamber. One of the walls, including the door, may include a window capable of blocking all or more than 90% of the UV-radiation from the one or more ultraviolet light bulbs while allowing a person to view the sterilization area during use, or one of the walls may include a window capable of blocking 98% or more of the UV-radiation from the one or more ultraviolet light bulbs while allowing a person to view the sterilization area during use. The window may include a small shutter or door that can close over the window. The walls may be constructed of multiple layers. The walls may be constructed of an outer wall layer that forms an outside surface of the sterilization chamber, and an inner wall layer including an opening through which the one or more ultraviolet light bulbs extend. The inner wall layer may be positioned such that the one or more ultraviolet light bulbs extend further into the sterilization area than the inner wall layer, but any cords and a majority of any light fixture are between the inner wall layer and the outer wall layer. The corrugated reflective material may be integral with the inner wall layer, or the corrugated reflective material may be separate from the inner wall layer and lines the inner wall layer. A floor of the sterilization chamber may be made of a smooth reflective material. A ceiling of the sterilization chamber may be made of a smooth reflective material and may include one or more ultraviolet light bulbs in a similar configuration to that of the walls.

An ultraviolet-transparent protective material may be installed over the one or more ultraviolet light bulbs in the sterilization chamber, the protective material configured to prevent damage to the one or more ultraviolet light bulbs. The ultraviolet-transparent protective material may be placed as an additional inner wall layer and entirely cover one or more of the walls inside the sterilization area. The ultraviolet-transparent protective material may be placed as casing sized to fit around only one of the one or more ultraviolet light bulbs, i.e., configured/sized to protect and fit around the light bulb and/or light fixture without extending to cover the full wall. The ultraviolet-transparent protective material may be installed over the one or more ultraviolet light bulbs installed on the floor, the protective material extending over the entire surface of the floor and configured to prevent damage to the one or more ultraviolet light bulbs installed on the floor and support the weight of objects placed in the sterilization area for sterilization.

The one or more ultraviolet light bulbs of the sterilization chamber may be adjustable in the sterilization chamber, such that a user may adjust the position of the one or more ultraviolet light bulbs into a desired position. The power level of the ultraviolet light radiating from the one or more ultraviolet light bulbs into the sterilization area may be adjustable. Multiple ultraviolet light bulbs may be attached to one or more of the walls inside the sterilization area, and the power level of the ultraviolet light radiating from the multiple ultraviolet light bulbs into the sterilization area may be adjustable by turning on different numbers of the multiple light bulbs (e.g., while leaving some lights off).

The control unit of the sterilization chamber may include a processor, memory, and software, wherein the software allows the user to select pre-programmed sterilization programs for different types of equipment to be sterilized. The control unit may include a processor, memory, and software, wherein the software allows the user to select/adjust a power level of ultraviolet radiation in the sterilization area and adjust a time for sterilization.

In one embodiment, a method of sterilization comprises placing one or more items to be sterilized inside an interior of a sterilization chamber. The sterilization chamber may comprise of the features discussed above and/or relevant features discussed below, including walls enclosing a sterilization area, one or more ultraviolet light bulbs attached to one or more of the walls inside the sterilization area, wherein the one or more ultraviolet light bulbs are capable of irradiating germicidal ultraviolet light at sufficient levels to kill or render non-viable microorganisms exposed to the ultraviolet light, and a corrugated reflective material that lines an inside surface of the walls. The method may also include sterilizing the one or more items by turning on the one or more ultraviolet light bulbs inside the sterilization chamber and leaving them on for an amount of time sufficient to kill or render non-viable 100% or nearly 100% of the microorganisms on the one or more items, wherein ultraviolet light from the one or more ultraviolet light bulbs is reflected in many different directions by the corrugated reflective material such that non-uniform surfaces of the one or more items are exposed to the ultraviolet light. If the position of the ultraviolet light bulbs in the sterilization chamber is adjustable, the method may further comprise moving the ultraviolet light bulbs in the sterilization chamber to a desired location for sterilization.

In one embodiment, a portable sterilization apparatus, comprises a light hood shade and one or more ultraviolet light bulbs attached to the light hood shade, wherein the one or more ultraviolet light bulbs are capable of irradiating germicidal ultraviolet light at sufficient levels to kill or render non-viable microorganisms exposed to the ultraviolet light. The sterilization apparatus may include an angle adjustment capable of adjusting the angle of the one or more ultraviolet light bulbs relative to the ground, and/or controls to operate the one or more ultraviolet light bulbs. The sterilization apparatus may also include wheels attached to a base. The base may include a reflective panel to reflect ultraviolet light from the one or more ultraviolet light bulbs onto an underside of an object to be sterilized. The sterilization apparatus may include a height adjustment slide, wherein the height adjustment slide may be used to further adjust the angle of the one or more ultraviolet light bulbs relative to the ground and raise at least a portion of the one or more ultraviolet light bulbs higher from the ground.

The sterilization apparatus may include a first movable extension portion attached to a side of the light hood shade. The extension portion may be attached by a hinge or hinges to the side of the light hood shade. The sterilization apparatus may include a second movable extension portion attached to a different side of the light hood shade. The first and second extension portions can fold back at least partially behind the light hood shade to expose a greater area to ultraviolet light emitted from the one or more ultraviolet light bulbs or to fold down around the sides of the light hood shade such that they project at least partially forward of the light hood shade.

In one embodiment, a method of sterilization comprises moving a sterilization device adjacent to an object to be sterilized. The sterilization device may comprise any features of the sterilization apparatus discussed above and/or relevant features discussed below, including a light hood shade; one or more ultraviolet light bulbs attached to the light hood shade, wherein the one or more ultraviolet light bulbs are capable of irradiating germicidal ultraviolet light at sufficient levels to kill or render non-viable microorganisms exposed to the ultraviolet light; and/or an angle adjustment capable of adjusting the angle of the one or more ultraviolet light bulbs relative to the ground. The method may further comprise adjusting the angle of the one or more ultraviolet light bulbs relative to the ground such that when turned on, the one or more ultraviolet light bulbs will radiate a majority of the ultraviolet light emitted from the one or more ultraviolet light bulbs on the object to be sterilized. The method may further comprise sterilizing the object to be sterilized by turning on the one or more ultraviolet light bulbs and letting ultraviolet light radiate on the object to be sterilized. The sterilization device may include movable extension portions attached to sides of the light hood shade, and the method may further comprise moving the extension portions to a position forward of the light hood shade such that, when the one or more ultraviolet light bulbs are turned on, the extension portions will block at least some ultraviolet light from the one or more ultraviolet light bulbs from radiating to the sides of the unit and focus the at least some ultraviolet light on the object to be sterilized. The base may include a reflective panel to reflect ultraviolet light from the one or more ultraviolet light bulbs onto an underside of the object to be sterilized, and moving the sterilization device adjacent to the object to be sterilized may include moving at least a portion of the base underneath the object to be sterilized.

In one embodiment, a sterilization apparatus, comprises a base; a central tower portion attached to the base, wherein the central tower portion has multiple sides of equal size, wherein each of the multiple sides is constructed of a reflective material; and multiple ultraviolet light bulbs, each of the multiple ultraviolet light bulbs attached to a different one of the multiple sides, wherein the multiple ultraviolet light bulbs are capable of irradiating germicidal ultraviolet light at sufficient levels to kill or render non-viable microorganisms exposed to the ultraviolet light. The sterilization apparatus may also include a control unit to operate the one or more ultraviolet light bulbs. Each of the base, the central tower portion, and the multiple ultraviolet light bulbs may be constructed only of materials that are non-magnetic. The central tower portion may include a hinge along first side and a latching mechanism on an opposite, second side, such that the central tower portion may be opened to service an interior of the central tower portion. The base may include wheels on which the sterilization apparatus may be rolled to multiple locations.

In one embodiment, a method of sterilization comprises moving a sterilization device into a room to be sterilized. The sterilization device may comprise any features of the sterilization apparatus discussed above and/or relevant features discussed below, including a base; a central tower portion attached to the base, wherein the central tower portion has multiple sides of equal size, wherein each of the multiple sides is constructed of a reflective material; and multiple ultraviolet light bulbs, each of the multiple ultraviolet light bulbs attached to a different one of the multiple sides, wherein the multiple ultraviolet light bulbs are capable of irradiating germicidal ultraviolet light at sufficient levels to kill or render non-viable microorganisms exposed to the ultraviolet light. The method may further comprise sterilizing the room to be sterilized by turning on the one or more ultraviolet light bulbs and letting ultraviolet light radiate throughout the room to be sterilized. The sterilizing step may be done for an amount of time sufficient to kill or render non-viable any microorganisms on the item/object.

In one embodiment a sterilization apparatus, comprises a central portion having wheels attached to a floor-facing side of the central portion; and one or more ultraviolet light bulbs attached to the floor-facing side of the central portion, wherein the one or more ultraviolet light bulbs are capable of irradiating germicidal ultraviolet light downward from the central portion toward the floor at sufficient levels to kill or render non-viable microorganisms exposed to the ultraviolet light. The wheels may be attached to extensions or legs extending from the floor-facing side of the central portion. The extensions or legs may be adjustable to raise or lower the wheels relative to the central portion. The central portion may further comprise an attachment point to which a line may be attached to pull the sterilization apparatus across a floor to be sterilized.

The central portion may further comprise one or more wing portions attached to the central portion, the one or more wing portions including one or more ultraviolet light bulbs attached to the one or more wing portions. The one or more wing portions may be attached to side edges of the central portion and may be able to articulate with respect to the central portion through a range of positions. The one or more wing portions may be locked in various positions of the range of positions.

In one embodiment, a method of sterilization comprises positioning a sterilization apparatus in a first region of a floor to be sterilized. The sterilization apparatus may comprise any features of the sterilization apparatus discussed above or relevant features discussed below, including a central portion having wheels attached to a floor-facing side of the central portion; and one or more ultraviolet light bulbs attached to the floor-facing side of the central portion, wherein the one or more ultraviolet light bulbs are capable of irradiating germicidal ultraviolet light downward from the central portion toward the floor at sufficient levels to kill or render non-viable microorganisms exposed to the ultraviolet light. The method may further comprise activating the one or more ultraviolet light bulbs to irradiate the germicidal ultraviolet light on the region of the floor to be sterilized. The method may further comprise moving the sterilization apparatus over the floor to a second region of the floor to expose the second region of the floor to the germicidal ultraviolet light. The step of moving the sterilization apparatus over the floor may be achieved by pulling a line attached to the sterilization apparatus, and/or by using a motor to move one or more of the wheels in the direction of the second region.

If the sterilization apparatus comprises one or more wing portions attached to the central portion, and the one or more wing portions include one or more ultraviolet light bulbs attached to the one or more wing portions, the method may include adjusting the one or more wing portions to a desired angle relative to the central portion prior to moving the sterilization apparatus over the floor. Optionally, the one or more wing portions may be adjusted to a desired angle relative to the central portion while moving the sterilization apparatus over the floor, especially where the one or more wing portions are automated so they may be moved by controls from a distance. Various floors or ground area may be sterilized with this method, including the floor of a food transportation trailer, the floor of a hospital or medical facility, the floor of a restaurant, etc.

In one embodiment, a sterilization apparatus, comprising a central portion having wheels attached to a side of the central portion; and one or more ultraviolet light bulbs attached to a central portion (e.g., to an upper side of a central portion), wherein the one or more ultraviolet light bulbs are capable of irradiating germicidal ultraviolet light upward from the central portion toward the underside of an item or object at sufficient levels to kill or render non-viable microorganisms exposed to the ultraviolet light. The sterilization apparatus may have wheels, attached to extensions extending from the side of the central portion, that are adjustable to raise or lower the wheels relative to the central portion. The central portion of the sterilization apparatus may further include an attachment point to which a handle may be attached to maneuver the sterilization apparatus underneath an item or object to be sterilized. The handle may be attached to the central portion by an articulated joint so that the handle may move through a range of positions with respect to the central portion. The wheels may be able to extend or telescope such that the wheels can be changed between configurations in which the wheels are closer together and configurations in which the wheels are further apart, e.g., the axle may be able to telescope to extend and/or retract.

In one embodiment, a method of sterilization comprises positioning a sterilization apparatus in a first region to be sterilized, the sterilization apparatus may include any features of the sterilization apparatus discussed above or relevant features discussed below, including: a central portion having wheels attached to a side of the central portion; and one or more ultraviolet light bulbs attached to the central portion (e.g., to an upper-side of the central portion), wherein the one or more ultraviolet light bulbs are capable of irradiating germicidal ultraviolet light upward from the central portion toward the underside of an item or object at sufficient levels to kill or render non-viable microorganisms exposed to the ultraviolet light. The method may further comprise activating one or more ultraviolet light bulbs to irradiate the germicidal ultraviolet light on the region of the area to be sterilized; moving the sterilization apparatus to a second region to expose the second region of the underside of an item or object to the germicidal ultraviolet light. Moving the sterilization apparatus over from one region to another is done by pushing or pulling the handle attached to the sterilization apparatus. The area to be sterilized may include the underside of a chair or cabinet. The method may include adjusting the distanced between the wheels to fit under different sized objects or areas to be sterilized.

BRIEF DESCRIPTION OF THE DRAWINGS

The disclosed devices/apparatuses, systems and methods can be better understood with reference to the following drawings. The components in the drawings are not necessarily to scale.

Figure 1:
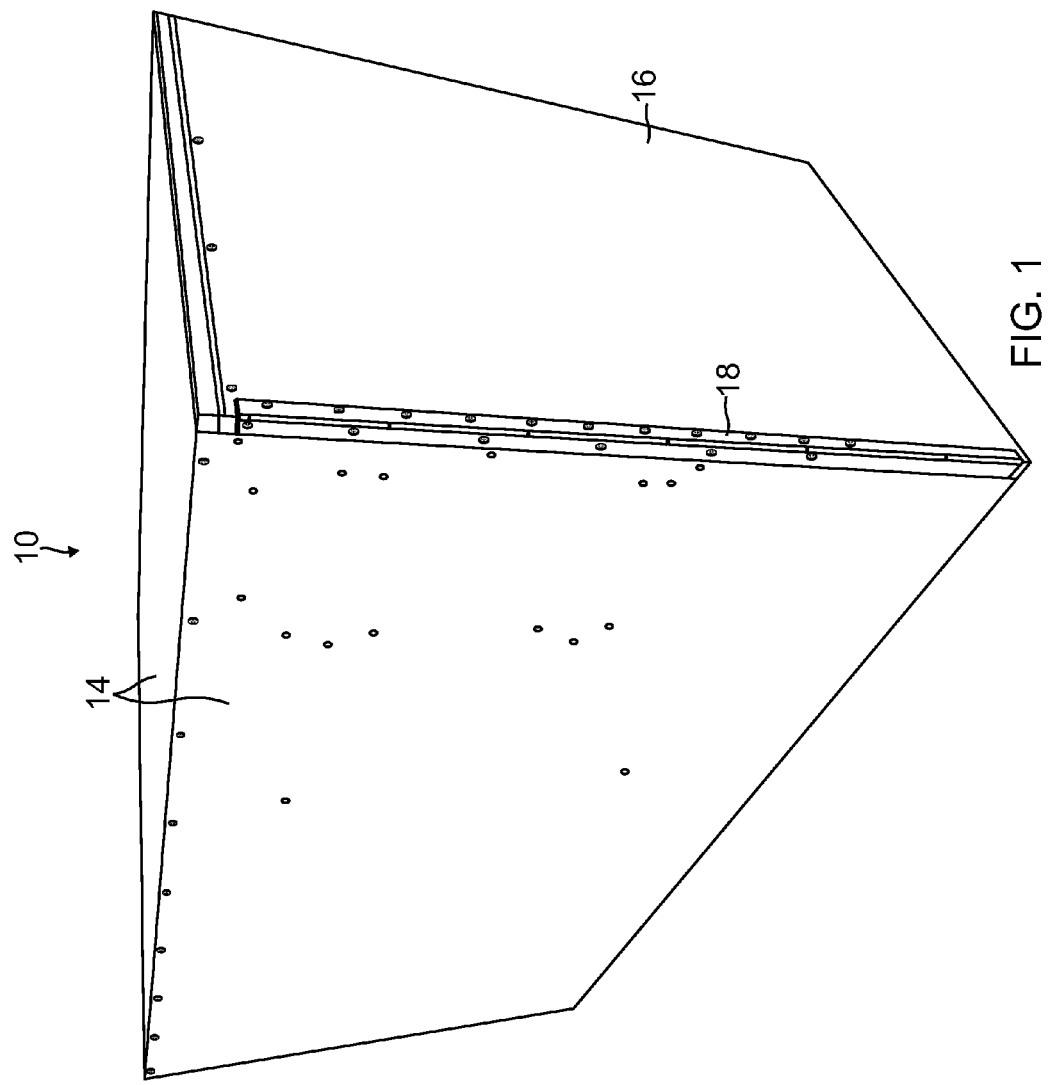
FIG. 1 shows an external view of an exemplary UV sterilization chamber.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

The following description and accompanying figures, which describe and show certain embodiments, are made to demonstrate, in a non-limiting manner, several possible configurations of ultraviolet sterilization devices/apparatuses and systems, and various methods of sterilization according to various aspects and features of the present disclosure.

Various systems, devices/apparatuses, and methods are described herein, including ultraviolet sterilization systems and devices for use in sterilizing equipment, e.g., sterilizing hospital equipment. While specific embodiments are discussed below by way of example, the embodiments and examples described are not intended to be limiting. The inventive principles associated with the embodiments described herein, including with respect to the chambers, units, systems, apparatuses, methods, etc. described herein, may be applied to a variety of uses, systems, apparatuses, units, methods, etc.

Figure 2:
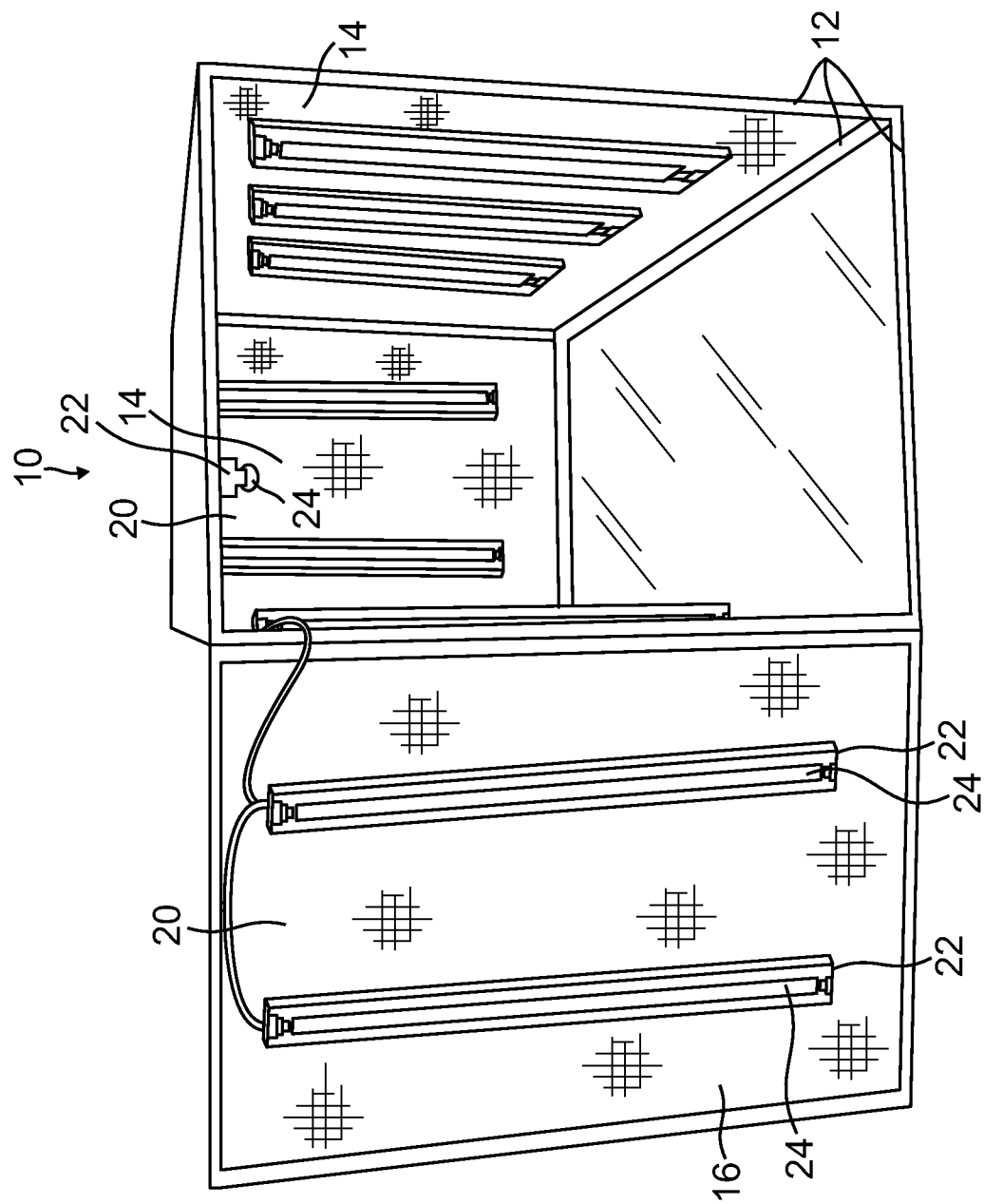
FIG. 2 shows an external view of the exemplary UV sterilization chamber of FIG. 1 with the door open to reveal the interior of the exemplary UV sterilization chamber of FIG. 1.
Figure 3:
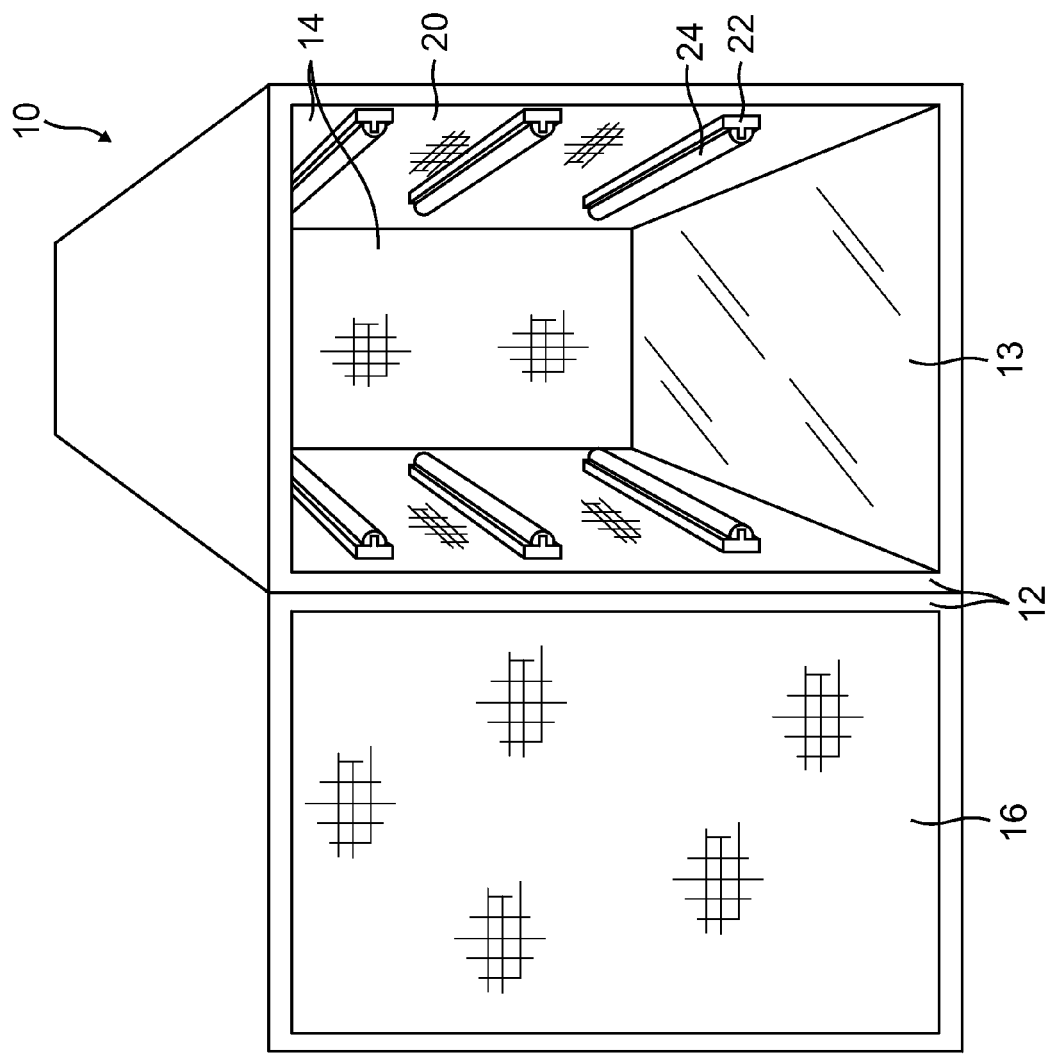
FIG. 3 shows an internal view of another exemplary UV sterilization chamber inside which equipment may be loaded for sterilization.

FIGS. 1-2 show an ultraviolet sterilization chamber or box 10 for sterilizing equipment. FIG. 3 shows a similar ultraviolet sterilization chamber or box 10 for sterilizing equipment of a somewhat different configuration. The ultraviolet sterilization chamber 10 can be made in a variety of sizes and shapes, but is preferably sized and shaped to be large enough to enclose and sterilize large equipment, e.g., hospital gurneys, carts, wheelchairs, waiting room chairs, hospital beds, and/or other large furniture or equipment. In one embodiment, the ultraviolet sterilization chamber 10 is 2-7 feet wide, 3-7 feet tall, and 5-10 feet deep. In one embodiment, the ultraviolet sterilization chamber 10 is 3 feet wide, 4 feet tall, and 7 feet deep. While the present embodiment of the sterilization chamber 10, shown in FIG. 1, has a rectangular cross sectional area, it is appreciated that a variety of cross sectional shapes fall within the scope of the present disclosure, including circular, decagonal, nonagonal, octagonal, heptagonal, hexagonal, pentagonal, or square. The ultraviolet sterilization chamber 10 may irradiate germicidal ultraviolet-C ("UV-C") wavelengths of light (e.g., wavelengths between 180 and 285 nanometers) into the interior of the chamber 10. In one embodiment, the wavelength of the UV-C light used in chamber 10 is at or around 253.7 nanometers. UV-C light is germicidal and deactivates microorganisms (e.g., breaks or renders their DNA non-viable), including microorganisms that cause diseases such as measles, tuberculosis, and influenza as well as viruses. Once the DNA of the microorganism is broken or rendered non-viable, the microorganism can no longer reproduce and is rendered harmless.

The ultraviolet sterilization chamber 10 may include one or more of the following: a sturdy frame, a door, walls, a floor, a ceiling, corrugated insulation, and/or ultraviolet light emitting light bulbs. The frame 12 of the chamber 10 may be constructed of steel, aluminum, or another suitably strong and sturdy material that resists damage from UV radiation. Preferably, the material of the frame 12 is aluminum or another non-magnetic material to make the chamber 10 lighter and to eliminate or limit the magnetic properties of the chamber. The term "magnetic" as used herein refers to a material that is attracted to a magnet, whereas the term "non-magnetic" refers to a material that is not attracted to a magnet. While the chamber 10 may be constructed using materials with magnetic properties, it is preferable to construct the chamber with non-magnetic materials so that the chamber can be used in the vicinity of magnetic resonance imaging (MRI) equipment without causing complications for the MRI equipment. Even the light fixtures 22 may be constructed with plastic ends to avoid using magnetic materials. However, if ultraviolet sterilization chamber 10 is not to be used in the vicinity of MRI equipment other metal materials, including those that are magnetic, may be used.

Walls 14 may be constructed of steel, aluminum, or another suitably strong and sturdy material that resists damage from UV radiation. Preferably, the material of the walls 14 is aluminum or another non-magnetic material to make the chamber 10 lighter and to eliminate or limit the magnetic properties of the chamber. As discussed above, it is preferable to construct the chamber with non-magnetic materials so that the chamber can be used in the vicinity of magnetic resonance imaging (MRI) equipment without causing complications for the MRI equipment. Walls 14 may be riveted or otherwise attached to the frame. Optionally, the walls may be attached to each other, e.g., if no frame is used. Again, it is preferable that the rivets, screws, or other attachment devices are made of non-magnetic material, although, magnetic materials may be used in some embodiments. Preferably, the walls 14, floor 13 and ceiling 15 form a fully enclosed chamber or a chamber that is fully enclosed when attached to a closed door 16. The top or ceiling 15 and bottom or floor 13 of the chamber 10 may also be considered part of walls 14. The bottom or floor 13 may be reinforced or use a stronger or thicker material to provide added support to heavy equipment or furniture placed in the chamber 10 for sterilization. The ceiling 15 may be constructed in a similar way to the walls 14 as discussed above.

The door 16 may also be considered a wall of the chamber 10. The door 16 may be attached to the frame or another wall by a hinge 18 as shown in FIG. 1. However, the door 16 may also be attached to the frame or the remainder of the chamber 10 by other means, or by hinges along another side of the door 16. In one embodiment, the chamber 10 may include a sliding door, instead of or in addition to a hinged door. The door 16 may be made of the same or a different material from the rest of the walls 14 of the chamber 10. For example, the door 16 may be made of steel, aluminum, or another suitably strong and sturdy material that resists damage from UV radiation. The door preferably allows for large equipment or furniture to enter the chamber 10 for sterilization and then closes the chamber to keep the UV radiation within the chamber. The door may latch or otherwise be held closed during sterilization.

The door (or another wall) may optionally include a transparent window made of UV-radiation blocking material, e.g., adequately tinted glass or transparent plastic or glass/plastic that has been treated to prevent or limit UV-radiation from passing through the glass or plastic. The window allows an operator of the chamber 10 to look into the interior of the chamber to see the equipment being sterilized or determine whether any UV light bulbs have burned out and need to be replaced. The window may have a small shutter or door that closes over the window when not looking into the chamber or to protect the window. The small shutter or door may be hinged to open or close over the window or the small shutter or door may be a sliding door that slides into place in front of the window when closed.

The interior of the chamber 10, e.g., including walls 14, ceiling 15 and door 16, is preferably lined with a reflective corrugated or otherwise patterned inner lining or insulation material 20, e.g., a corrugated aluminum insulation material, corrugated steel material, aluminum foil, patterned reflective Plexiglas, or another patterned or corrugated reflective material. The reflective corrugated or otherwise patterned material is very beneficial in that it reflects the UV light in the chamber 10 in many different directions, which helps spread the light on every surface of the equipment, furniture, etc. being sterilized in the chamber 10. Often, the equipment, furniture, etc. to be sterilized has a non-symmetrical, non-uniform, and/or non-even shape with varied surface types. It can be difficult to sterilize such equipment because the varied shapes of the equipment and surfaces can create shadowed areas on the equipment or in grooves on the surface of equipment. The shadowed areas may not receive enough UV light to sterilize the shadowed area, which can leave the equipment, furniture, etc. not fully sterilized. By lining the interior of chamber 10 with a reflective material that is corrugated or patterned to reflect the UV light in all or nearly all directions, 100% or nearly 100% (e.g., 98-100%) sterilization of the equipment, furniture, etc. may be sterilized. In other words the patterned or corrugated material is able to reflect the light in so many different ways that no shadowed portion of the equipment, furniture, etc. is left unexposed to the UV light. Indeed shadowed portions are avoided because the UV light is reflected in all directions. A good pattern or corrugation design will reflect light in essentially every direction within the chamber 10 and can result in 100% sterilization of even unique shaped or non-evenly shaped surfaces of equipment, furniture, etc. Another benefit having a corrugated or otherwise patterned reflective lining material is that it allows for more variations in the design and arrangement of the UV lights in the chamber, i.e., because the light will be reflected so thoroughly in all or nearly all directions. For example, lights may not need to be arranged evenly around the item being sterilized, and shadowed areas may be prevented from forming with fewer light than might otherwise be required.

The corrugations/pattern on the reflective lining or insulation material 20 may be arranged in a random or pseudo-random pattern to ensure that the UV light is reflected in all or nearly all directions. However, other designs or patterns are also possible as long as the UV light is reflected in many different directions sufficient to achieve 100% or nearly 100% sterilization on un-even surfaces and non-uniform shaped equipment, furniture, etc. For example, a pattern of concentric circles, wavy lines, wrinkles, small protrusions (e.g., circular, triangular, oval, trapezoidal protrusions), and/or crisscrossing lines may be used. A repeating pattern of small corrugation shapes may be used. Some crosshatching is shown on the walls in FIGS. 2-3 as representative of various corrugations/patterns that may be used on the walls. For convenience and to avoid making the figures overly complex or cluttered with lines, the crosshatching is only shown on portions of the walls, but the pattern can cover a portion or cover the entire wall or most of the wall for each of the walls of the chamber. A pattern of a logo, e.g., a company logo, may also be formed on the lining or insulation material 20; however, this works best when the remainder of the pattern on the lining or insulation material 20 is better designed for reflecting light in all or nearly all directions.

The floor 13 of the chamber 10 is shown in FIGS. 2-3 as being made of a reflective material (e.g., a mirror, reflective Plexiglas, or mirror-like material). The reflective floor material helps ensure that the underside of the equipment, furniture, etc. gets sterilized as well as the top and sides thereof. Having the reflective floor surface be smooth makes it easier to slide the equipment, furniture, etc. into the chamber 10. However, the reflective floor material may also be corrugated or otherwise patterned as discussed above.

Optionally, the walls 14, ceiling 15 and floor 13 may be formed of layers of material. For example, walls 14, ceiling 15 and floor 13 may be formed of an inner wall and an outer wall, or an inner wall, outer wall, and corrugated insulation/lining layer. In FIGS. 1-3, the walls 14 are formed with a layer of flat wall material (e.g., an aluminum sheet), and an inner layer of corrugated insulation (e.g., corrugated aluminum insulation). Optionally, another inner wall layer may be included between the lining/insulation layer 20 and the outer wall layer.

In one embodiment, an outer wall layer forms the outside wall of the chamber 10, and a light fixture (e.g., light fixture 22) may be mounted on the internal side of the outer wall. An inner wall layer is formed in chamber 10 inside of the outer wall layer. The inner wall layer may include an opening through which a light bulb (e.g., UV light bulb 24) mounted in the light fixture (e.g., UV light fixture 22) extends. The inner wall layer may be flush with the innermost edge (i.e., inside the chamber 10) of the light fixture 22, or may cover a portion of the innermost edge of the light fixture. When viewed inside the chamber 10, only the light bulbs will protrude from the inner wall layers into the chamber 10 (contrast this with the embodiment shown in FIG. 2, in which the light fixture 22 and the light bulb 24 both protrude from the walls into the interior of the chamber 10). Any cords or other electronics associated with the light fixtures or other parts of chamber 10 may pass between the inner walls and the outer walls without being visible when looking into the chamber. The inner walls may be removable to service the light fixtures, cords, or other electronics. The inner walls may be formed of or lined with corrugated or otherwise patterned reflective lining/insulation material as discussed above to better distribute the light in the sterilization chamber. The materials used for the walls and insulation may be the same as those discussed previously.

Optionally, a UV transparent protective material (e.g., glass, Plexiglas, plastic, or metal frame or mesh) layer may be installed over the light bulbs (e.g., UV light bulbs 24). This protective material can help prevent damage to the UV light bulbs and thereby prevent injury to the user from cuts or electrocution associated with broken bulbs. Preferably, the protective material is generally transparent to UV radiation and does not substantially hinder the required amount UV radiation from reaching and effectively sterilizing the equipment, furniture, item, etc. to be sterilized. If necessary, higher power UV light bulbs may be used so that a sufficient amount of UV radiation passes through the protective material for sterilization, even if some UV radiation is blocked by the protective material. The UV transparent protective material may be placed as an additional inner wall layer and entirely cover one or more inner walls (including any corrugated or otherwise patterned lining/insulation) of the chamber 10, the door 16, the ceiling, and/or the floor. If a strong enough material is used on the floor (and the material/panel is well enough supported to hold it above the light bulbs and protect them, e.g., with supports and/or support beams (preferably reflective or UV transparent) spaced at various locations on the floor and/or along the edges), UV light bulbs may be installed on the floor under the UV transparent protective material (e.g., a panel of the protective material), so that light bulbs may be positioned underneath any equipment, furniture, items, etc. placed in the chamber 10 for sterilization. This helps ensure the bottom of the equipment, furniture, items, etc. is fully sterilized, i.e., even the legs or base that sits on the UV transparent protective material of the floor will be sterilized because the UV light can pass through the protective material to the surface of the equipment, furniture, items, etc., resting directly on the protective material. (This may be considered similar to light of a photocopier shining up through the glass to the surface of the paper resting on the glass). Optionally, the UV transparent protective material may be a narrower material or casing that primarily covers the exterior of the bulbs without extending along the entire length of the wall. The UV transparent protective material is preferably removable to change the light bulbs and service the light fixtures or other equipment.

Light fixtures 22 and light bulbs 24 may be arranged throughout the chamber 10 in a variety of ways. As discussed above, having a corrugated or otherwise patterned reflective lining/insulation allows for more freedom in designing the arrangements of lights (e.g., because the light will be reflected to all necessary locations). FIG. 2 shows an arrangement in which the light fixtures 22 and UV light bulbs 24 are arranged vertically on the side walls with three light bulbs on each of the long sides and two light bulbs on the end side and door, while the top or ceiling 15 also has two light bulbs arranged lengthwise thereon. However, other numbers of UV light bulbs and other arrangements are also possible. For example, FIG. 3 shows another arrangement of light bulbs in which the light bulbs are generally arranged horizontally on the side walls. Preferably, the light bulbs 24 will be evenly spaced around the chamber; however, if the reflective lining properly reflects the UV light, an even spacing is not necessary. The UV light bulbs 24 may be between 6 inches and 60 inches long, more preferably the UV light bulbs 24 are between 24 inches and 48 inches long. In one embodiment the UV light bulbs 24 are 48 inches long. Alternatively, the UV light bulbs 24 may consist of an array of UV sterilization compact fluorescent lamps (CFL), (similar to an 'energy saver bulb'). It will be obvious to a person of ordinary skill in the art that a variety of arrangements of the CFL array (e.g. a grid layout, a diamond layout, a hexagonal or 'honey comb' lay out) are possible and fall within the scope of the present disclosure.

The light fixtures and bulbs (e.g., fixtures 22 and bulbs 24) shown in the figures herein are merely representative, and are not meant to be restrictive. The light fixtures and bulbs ultimately used may be in any format, shape, or size described herein or shown with respect to any of the embodiments, e.g., the fixtures 22 and bulbs 24 may be similar to fixtures 122 and bulbs 124 shown in FIG. 7 or the fixtures and bulbs of other figures. In one embodiment, the bulbs may have a similar shape and size to fluorescent light bulbs.

Optionally, the lights may be movable or adjustable in the sterilization chamber, e.g., such that a user may move the lights into a position to better focus the light in a desired region. To do this the light fixtures may be installed on mounts, panels, runners, and/or tracks that allow the lights to translate/slide forward or backward (e.g., horizontal) along the walls of the chamber 10. Optionally, the light fixtures may be able to translate/slide upward or downward (e.g., vertical) as well as or instead of sliding forward or backward (e.g., horizontal). Optionally, the light fixtures may be installed on a rotating mount or panel such that the light fixtures and the light bulbs may be rotated from vertical to horizontal or any angle in between. The rotation may be in a range of 90°, 180°, 360°, or another range. If UV transparent protective material is used to cover the light bulbs as discussed above, the UV transparent protective material may be removable to allow manual adjustment of the lights. Further, if the lights are movable or adjustable, corrugated or otherwise patterned lining/insulation may not be used as movement of the lights may be effective to prevent any shadowed areas on the object being sterilized; however, the corrugated or otherwise patterned lining/insulation can still be effective in helping improve light exposure even when the lights are adjustable or movable.

Optionally, the movement (e.g., translation horizontally or vertically, and/or rotation as discussed above) of the lights may be automated and controlled by a control unit and/or software. For example, the lights may move along the walls of the chamber 10 similar to how a photocopier light moves. The pattern of movement may be programmed into a computer, control unit, and/or software run on a computer/control unit to control the movement of the lights. The movement of the lights can be designed to ensure that all areas of the item being sterilized have been sufficiently exposed to the UV radiation to kill or render non-viable any microorganisms thereon. If lights are installed in the floor under a sturdy UV transparent protective material that covers the floor, as discussed above, the lights in the floor may move under the equipment, furniture, item, etc. to be sterilized (e.g., similar to a photocopier light moving under the glass) such that the entire bottom of the equipment, furniture, item, etc. is exposed to the UV radiation sufficiently to kill or render non-viable any microorganisms, even those on the legs or base of the equipment, furniture, item, etc. resting on the UV transparent protective material.

The UV light bulbs 24 may be germicidal bulbs of various power levels. For example, the UV light bulbs 24 may be in a range of 30 watt to 200 watt bulbs. Optionally, the UV light bulbs 24 may be in a range of 40 watt to 75 watt bulbs. The UV light bulbs 24 may optionally be T8 or T5 bulbs. The UV light bulbs are germicidal to kill or render non-viable microorganisms including bacteria and viruses. If the bulbs operate at a higher power, then it takes less time to sterilize items and kill or render non-viable microorganisms. If the bulbs operate at a lower power, then it takes more time to sterilize items and kill or render non-viable microorganisms, (i.e., the light must shine on the item being sterilized for a longer time period). Optionally, a sensor or multiple sensors may be used to indicate whether a bulb has stopped working and needs to be replaced. In one embodiment, a sensor may be used that detects the intensity of the light or power in the chamber and can sense changes in intensity if a bulb burns out or stops working.

The sterilization chamber 10 may be designed for adjustable power settings for different sterilization needs or to accommodate the material properties of the various items to be sterilized. Some materials may melt or be otherwise damaged if exposed to high powered UV radiation, so it may be desirable to use lower power UV light when sterilizing these items. However, some materials are more durable (less likely to be damaged) under UV radiation and can be sterilized much faster if higher power UV light is used. Accordingly, the light fixtures 22 may be designed such that the UV light bulbs 24 may be easily interchangeable, such that higher watt bulbs may be installed in the light fixtures and used for sterilizing more durable items, and lower watt bulbs may be installed in the same light fixtures and used for sterilizing items that might melt or be otherwise damaged in high powered UV light (i.e., the bulbs may be exchanged to meet the needs of the sterilization and the items to be sterilized). Also, the sterilization chamber 10 may include a certain number of bulbs, but may be designed to allow only some of the lights to be turned on for lower powered sterilization, while more of the lights or all of the lights might turn on for higher powered sterilization. The number of lights turned on and active may be varied to achieve the desired overall UV power level inside the chamber. Optionally, there may be some light bulbs of a lower watt level and some light bulbs of a higher watt level installed together inside the chamber (or bulbs with a range of watt levels may be installed together in the chamber). The lower watt UV light bulbs may be turned on and the higher watt UV light bulbs turned off for a lower powered sterilization. For a higher powered sterilization, the high watt UV light bulbs may be turned on and the low watt UV light bulbs may be turned off or remain on. Again the number of bulbs turned on may be varied for different sterilization or material needs.

The sterilization chamber may include a user interface or control panel to allow a user to adjust the settings of the sterilization chamber 10, e.g., a user may use a button(s), a switch(es), a dial(s), a touch screen, a remote control, a wireless device, and or other controls to control the sterilization chamber 10. Some controls may allow a user to set the power level desired in the sterilization chamber and/or set how long the sterilization should last. For example, the user may be able switch on or off a series of switches, where each switch will turn on or off some of the UV light bulbs in the sterilization chamber. By turning on or off the desired number of switches, the user may control power level within the sterilization chamber. Optionally, a dial, multiple dials, a button, or multiple buttons may be used to turn on or off some or all of the lights in the sterilization chamber. A timer may be used that automatically shuts off the lights after the sterilization time has been completed. The user may be able to adjust the time for sterilization according to the situation or item to be sterilized. In one embodiment, a dial is used that acts as a timer; the dial may be turned and set to a specific time. While the timer is counting, the UV light bulbs receive electricity and are turned on, but when the timer runs to zero, the electricity is cut off and the UV light bulbs turn off. Multiple such dials may be used to control different sets of lights.

Optionally, a more sophisticated control unit, control panel and/or computer may be used to control the sterilization chamber using software. The control unit, control panel and/or computer may include and/or use a processor, memory, and software. The software may be programmed such that a user may select the desired power level and the amount of time the sterilization should take place. The control panel and/or computer may provide the user with pre-programmed sterilization settings for different equipment or scenarios. In embodiments where automated movement of the lights is used, the control unit/computer may implement software to control the movement of the lights. The user may control where the lights move or pre-programmed sterilization programs/settings may move the lights in pre-determined patterns. The control unit/computer may provide instructions to the sterilization through a wired connection or wirelessly. Optionally, a smart phone application or "app" may be used to control the sterilization chamber.

The user interface, control unit, computer, etc. used may desirably be capable of controlling the sterilization chamber 10 from a remote location, so the user interface, control unit, computer, etc. may be kept away from any MRI equipment when sterilizing an MRI suite. For example, a control unit may have a long cord (e.g., 15-30 feet) and a long distance transformer, so it can be located outside an MRI suite while controlling and powering sterilization chamber 10 inside the MRI suite. It is appreciated that various methods of controlling the unit would fall within the scope of the present disclosure.

The sterilization chamber 10 may be portable. The sterilization chamber may have wheels on a bottom thereof to allow the sterilization chamber to be wheeled to a desired location. The sterilization chamber may be loaded into a bed of a truck or in a trailer and driven around to various locations. Optionally, the sterilization chamber may be formed in or as a trailer for a truck.

The sterilization chamber 10 may also be stationary and/or formed as a room in a building or lot. For example, the sterilization chamber 10 may be manufactured as a sterilization room in a hospital into which any equipment, furniture, items, etc. from the hospital or elsewhere may be moved into the sterilization room for sterilization. The sterilization room may include any of the features discussed above with respect to sterilization chamber 10, except it would not be portable. A sterilization room or chamber may include a moving conveyor belt, line, floor, or other feature for automated movement of equipment into, through, and out of the room to be sterilized.

Additional elements may be provided with the sterilization chamber 10 and/or inside the sterilization chamber 10 to aid sterilization. For example, one or more trays may be provided on which smaller equipment, instruments, tools, items, etc. may be placed for sterilization. The trays may be constructed of a UV transparent material (e.g., a Plexiglas, glass, or transparent plastic material) so that the undersides of the equipment, instruments, tools, items, etc. resting on the tray may be sterilized when the tray is placed in the sterilization chamber 10. Alternatively, the trays may be made of a reflective material or a corrugated reflective material. A cart may be provided in which the one or more trays may be loaded. The cart may have ledges along its sides so that the trays may be slid over the ledges and supported by the cart at the edges of the tray (i.e., so the bottom of the tray is not covered and the items on the tray may be sterilized from underneath). Multiple trays may be loaded into the cart on different layers of ledges. Optionally a suspension mechanism (e.g., suspended hooks, lines, straps, etc.) may be included that can allow equipment, instruments, tools, items, etc. to be suspended from the ceiling of the sterilization chamber leaving the bottom(s) of the equipment, instruments, tools, items, etc. fully exposed to the UV light. For example, a hook(s) may extend from the ceiling or be suspended from a loop and/or line on the ceiling and equipment, instruments, tools, items, etc. may be suspended from the hook(s). The hook(s) or other suspension mechanism is preferably transparent to UV light where possible.

Various methods of using the sterilization chamber 10 are possible. Often, the methods of use will involve one or more of the following steps, including opening the door 16 to the sterilization chamber 10, placing one or more items desired to be sterilized inside the interior of the sterilization chamber 10, closing the door 16 to the sterilization chamber 10, turning on the UV light bulbs inside the chamber and leaving them on for a desired amount of time (e.g., using a user interface/control unit/computer as discussed above), removing the item from the sterilization chamber 10. Power levels of UV light and times for sterilization may vary depending on the item being sterilized. A power level of UV light and time of exposure to the UV light may be selected such that 100% or nearly 100% of the microorganisms on the item are killed or rendered non-viable. If additional features among those discussed above are used, the method of use may involve using those features as discussed above (e.g., if the lights are adjustable, the lights may be moved to the desired location for sterilization).

Methods of manufacture may include assembling some or all of the various features described above with respect to the sterilization chamber 10.

Figure 4:
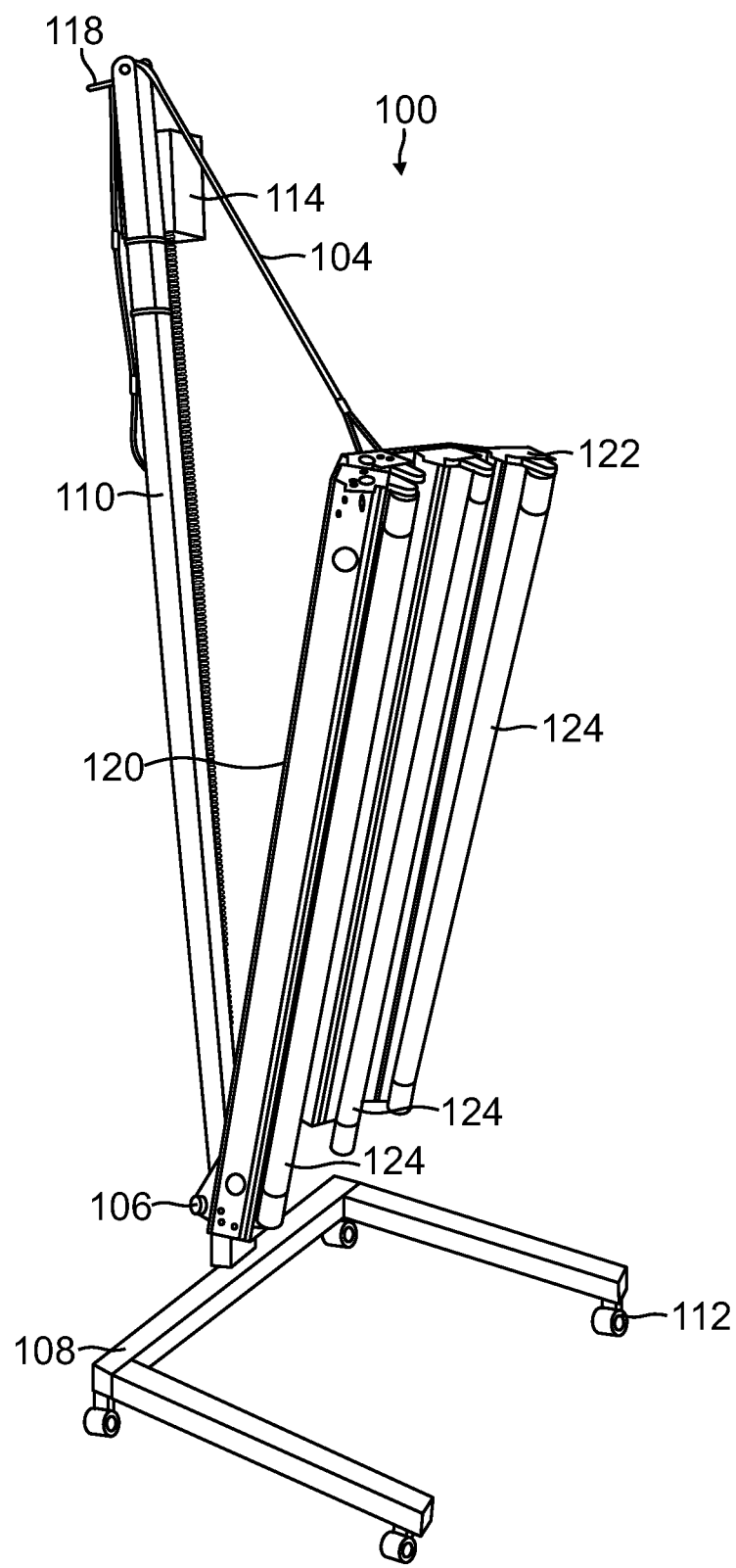
FIG. 4 shows a front view of an exemplary adjustable-angle, directed-light UV sterilization unit, with a high angle.
Figure 5:
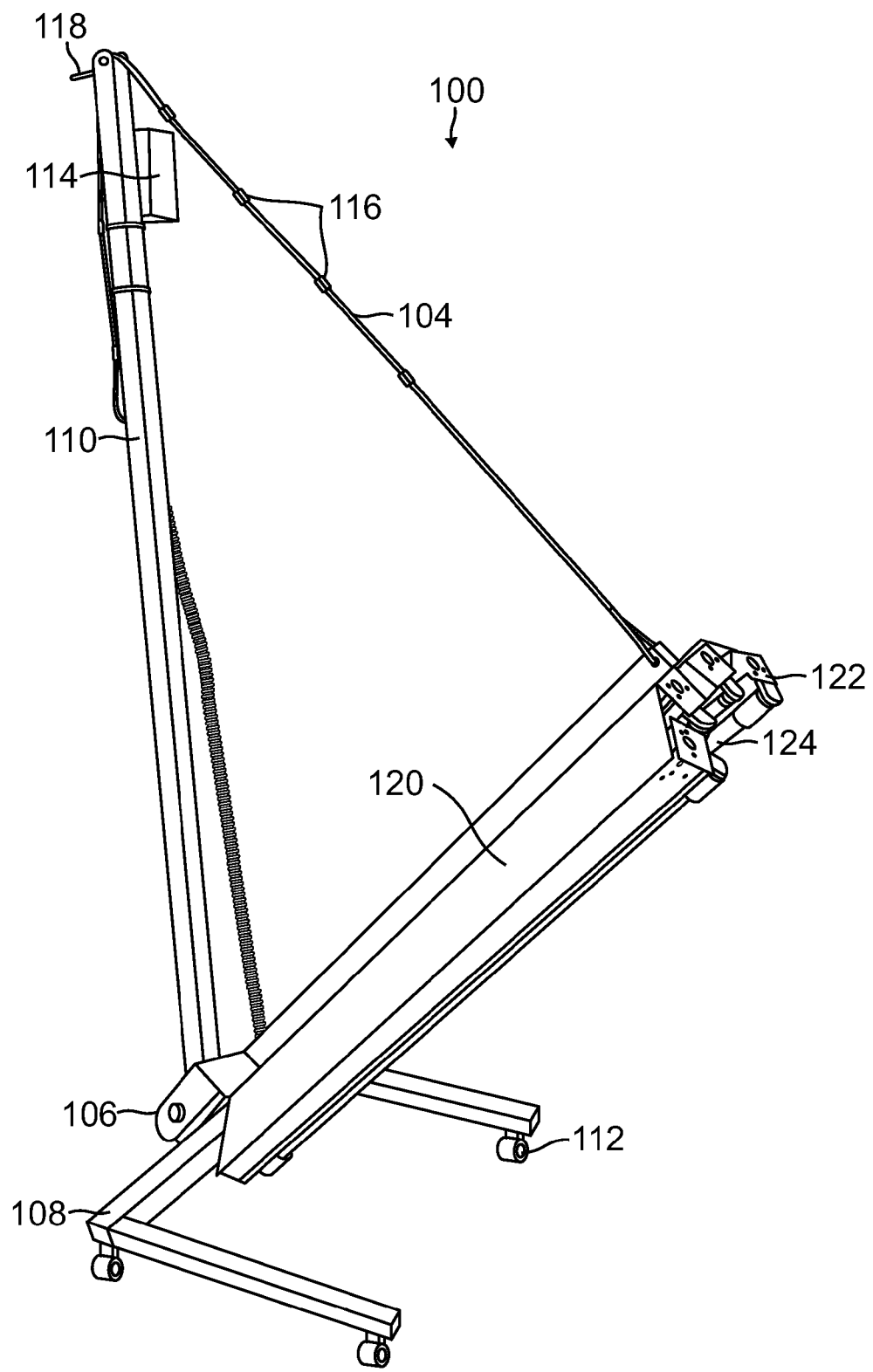
FIG. 5 shows another view of the exemplary adjustable-angle, directed-light UV sterilization unit of FIG. 4 with a lower angle than that shown in FIG. 4.
Figure 6:
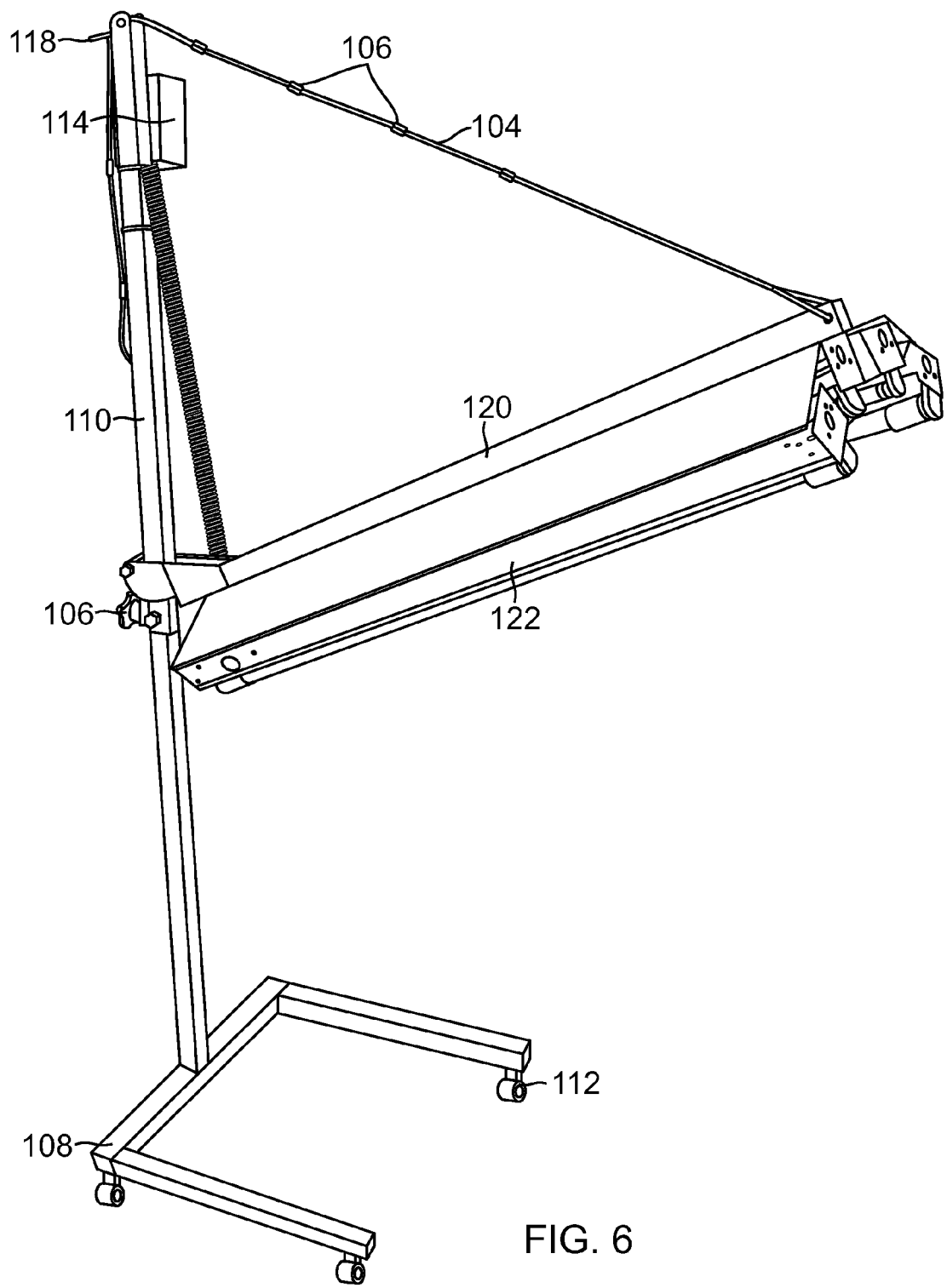
FIG. 6 shows another view of the exemplary adjustable-angle, directed-light UV sterilization unit of FIG. 4 with an elevated low angle.
Figure 7:
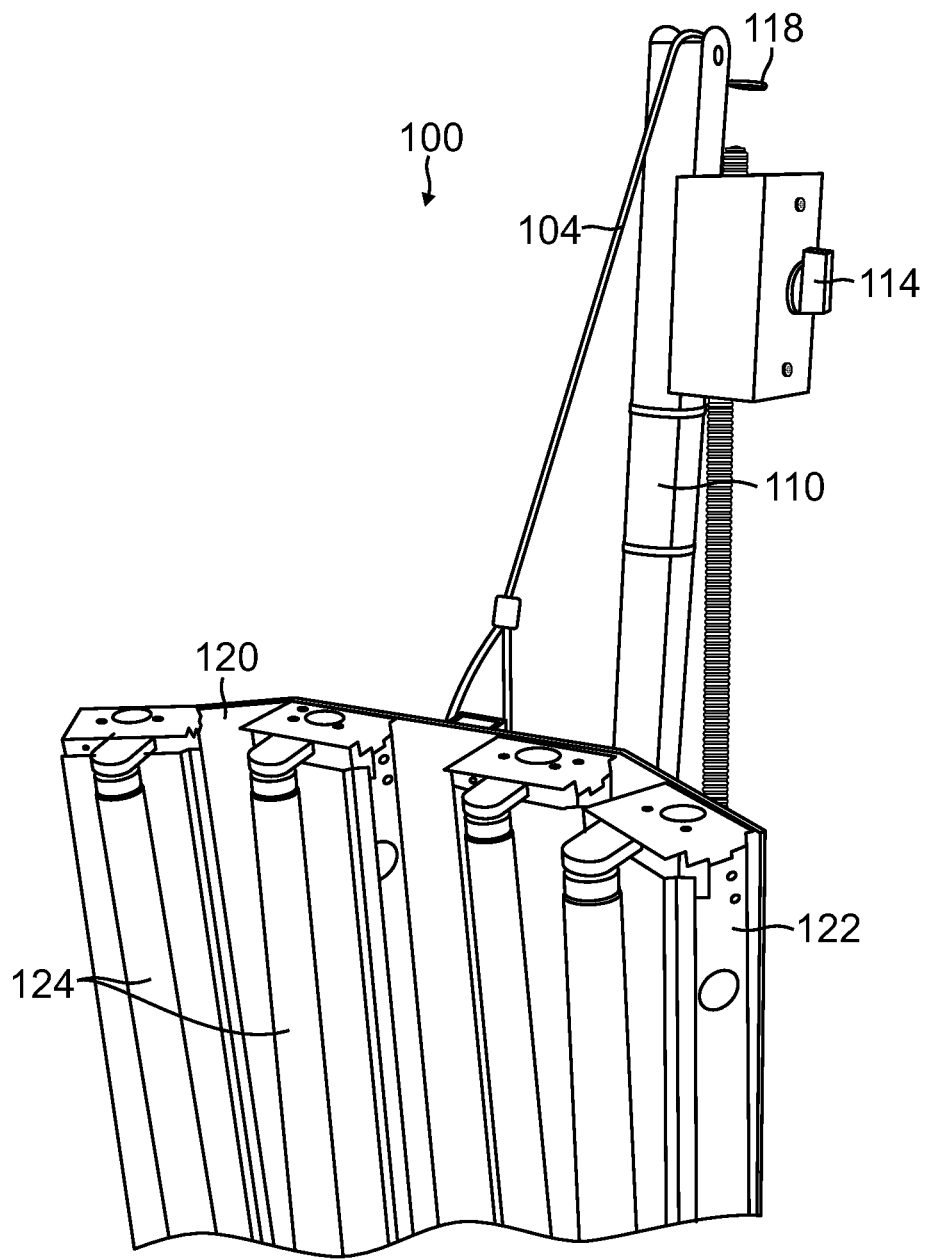
FIG. 7 shows a view of the upper portion of the exemplary adjustable-angle, directed-light UV sterilization unit of FIG. 4 and an exemplary control dial.

FIG. 4 shows an exemplary adjustable-angle, directed-light UV sterilization unit 100. FIGS. 5-7 show various views of an exemplary adjustable-angle, directed-light UV sterilization unit 100 similar to that shown in FIG. 4. FIGS. 4-7 show an adjustable-angle, directed-light UV sterilization unit 100 that includes a light hood shade 120, light fixtures 122, UV light bulbs 124, an angle adjustment 104, a height adjustment slide 106, a base 108, a vertical support 110, wheels 112 on the base, and a control unit 114. The UV sterilization unit 100 may be powered by a power cord (not shown).

Light hood shade 120 may be constructed of a sheet of steel, aluminum, or other material. The material of light hood shade 120 may be reflective to help direct light toward an object being sterilized. Optionally, the surface may be corrugated or otherwise patterned as discussed above. Light hood shade 120 may be shaped in various ways to direct the UV light as desired. As best seen in FIGS. 5-7, the light hood shade 120 may include a central flat portion and two side portions that are angled slightly with respect to the central portion (e.g., the side portions may be at a 15°-45° angle, or optionally a 20°-30° angle, or a 20° angle). This angling of the side portions helps direct and guide the light in the desired direction for sterilization, while helping to minimize or prevent the UV light from spreading very far to the sides or behind the light hood shade 120. Focusing the UV light on the object being sterilized while minimizing the spread of the UV light in other directions helps make the adjustable-angle, directed-light UV sterilization unit 100 safer for use in a room where people are present. For example, an emergency room or hospital waiting room may rarely if ever be completely free of people as patients may continually come in at any time of day. In some instances, some of the patients will have communicable diseases, be bleeding, and/or vomit in the waiting room, and may spread contaminated material to the waiting room furniture or other equipment or items with which they come in contact. This often necessitates sterilizing furniture, equipment, or other items/objects while other patients are still present in the emergency or hospital waiting room. Accordingly, having a sterilization unit that can focus light on a particular piece of furniture or a particular object without subjecting other people in the room to the UV radiation is very beneficial.

Optionally, additional wing or extension portions (not shown), which may optionally be made of reflective material, may be added to the sides of the light hood shade 120 to help further contain and direct the UV light in the desired direction while preventing UV light exposure in undesired areas. For example, wing or extension portions that are generally the same length (although they may be somewhat larger or shorter as well) as the light hood shade 120 may be attached by a hinge or hinges along the sides of the light hood shade 120. The hinges would allow the wing or extension portions to fold back behind the light hood shade 120 to expose a greater area to the UV light or to fold down around the sides of the light hood shade 120 to cover the sides of the light fixtures 122 and light bulbs 124 and focus the light in a narrower range as desired. The wing or extension portions may be wide enough that when they are in the forward position they block the majority of side light from the UV light bulbs 124 from escaping to the sides of the unit. The wing or extension portions may also allow the user to adjust the area that the light contacts by swinging the wing or extension portions wider for a wider area exposed to the UV light or narrower for a narrower area exposed to the UV light. The wing or extension portions help make the unit safer for use in a room where other people are present because it can narrow the focus of the light and prevent wide exposure as discussed above. For example, if a patient vomited on a waiting room chair, the sterilization unit 100 could be moved over to the chair, the base 108 rolled under the chair around or between the legs of the chair, the angle and height of the light hood shade 120 could be adjusted to match the chair, then the wing or extension portions could be swung down to cover the sides of the chair. When the sterilization unit 100 is turned on, the UV light will be focused primarily on the chair without exposing the surrounding people to the UV light. The wing or extension portions are preferably reflective on the side exposed to the light to help focus the light on the desired object for sterilization.

Light fixtures 122 are attached to the operative side or focal side of the light hood shade 120. Light fixtures 122 may be similar to the light fixtures 22 discussed above and have the same or similar features. UV light bulbs 124 may be used in the light fixtures 122. UV light bulbs 124 may be similar to the UV light bulbs 24 discussed above and have the same or similar features. Ultraviolet-transparent protective material similar to that discussed above may be installed over the one or more of the UV light bulbs 124. The UV light bulbs 124 may be between 6 inches and 60 inches long, more preferably the UV light bulbs 124 are between 24 inches and 48 inches long. In one embodiment the UV light bulbs 124 are 48 inches long. Alternatively, the UV light bulbs 124 may consist of an array of UV sterilization compact fluorescent lamps (CFL), (similar to an 'energy saver bulb'). It will be obvious to a person of ordinary skill in the art that a variety of arrangements of the CFL array (e.g. a grid layout, a diamond layout, a hexagonal or 'honey comb' lay out) are possible and fall within the scope of the present disclosure.

An angle adjustment 104 may be formed by a sturdy metal cord or other sturdy line or rope with notches or fixtures 116 thereon. The vertical support 110 may include a notch or groove 118 thereon (e.g., on an extension extending from near the top of the vertical support 110) in which the notches or fixtures 116 may be received to hold the angle adjustment 104 at the correct angle. FIGS. 5 and 6 show angle adjustment 104 adjusted such that the light hood shade 120 is set at a lower angle relative to the higher angle shown in FIG. 4. FIGS. 5 and 6 also show the fixtures 116 along a metal line/cord. To adjust the angle of the light shade hood the angle adjustment 104 may be set or locked into the notch/groove 118 at different points along the angle adjustment 104. In FIG. 4, the first fixture 116 of the angle adjustment 104 is set in the notch/groove 118; whereas in FIGS. 5 and 6, the fifth fixture 116 is set in the notch/groove 118. Other angle adjustments may also be used, e.g., angle adjustments using pulley systems, retractable lines, a coil and handle (e.g., the handle can wind/unwind a line around the coil to raise or lower the top of the light hood shade 120 to change the angle).

A height adjustment slide 106 that slides along the vertical support 110 may also be included in the sterilization unit 100. The height adjustment slide can be used to adjust the height of the bottom end of the light hood shade 120. This can help change the angle of the light shade hood and help it sterilized a higher surface. In FIG. 6, the height adjustment slide 106 is set at a mid-point on the vertical support 110 and the fifth fixture 116 of the angle adjustment 104 is set in the notch/groove 118; accordingly, the angle of light hood shade 120 in FIG. 6 is significantly lower than the angle shown in FIG. 4, but the lowest point of the light hood shade 120 is much higher than that shown in FIG. 4. In FIG. 5, the height adjustment slide 106 is at its lowest position and the fifth fixture 116 of the angle adjustment 104 is set in the notch/groove 118; accordingly, the angle of light hood shade 120 in FIG. 5 is lower than the angle shown in FIG. 4, but higher than that shown in FIG. 6.

The angle adjustment 104 and the height adjustment slide 106 work together to provide a wide variety of angle and height adjustments to the light hood shade 120 and the light bulbs 124 of sterilization unit 100. This allows the sterilization unit 100 to be customized to sterilize various types of equipment and furniture, and helps to focus the UV light in the desired sterilization location while preventing exposure to UV light outside of the desired sterilization location. It is appreciated that various methods of adjusting the height and angle of the adjustable-angle, directed-light UV sterilization unit 100 fall within the scope of the present disclosure, for example extension rod(s); joint(s); latch(es); hydraulic system, and/or a strap(s) and a peg(s) (e.g. where the strap may have holes that allows the strap to be set on the peg(s) at different lengths which allows different angles of the side or wing portions).

Base 108 provides support to the sterilization unit 100 and helps prevent the unit from tipping over. Wheels 112 may be used on the base to help make the sterilization unit 100 more portable/movable. The base 108 may include two leg portions that extend forward and provide added support to the sterilization unit to prevent tipping of the unit. The two leg portions may be longer than that shown in FIGS. 4-7. The two leg portions may also have an adjustable length (e.g., telescoping legs) so the legs can be extended to provide added support when the light hood shade 120 is set at a low angle (e.g., as shown in FIG. 6) and is more likely to tip the over. The base may also include a reflective panel (e.g., a mirror or mirror-like material) that extends between the two leg portions. This reflective panel or mirror may be pushed underneath a chair, other piece of furniture or equipment to be sterilized and may reflect the UV light onto the underside of the chair, other furniture, or equipment to sterilize underneath the item. The reflective panel may be angled to better reflect the light or may include an angled portion and a flat portion.

As best seen in FIG. 7, the sterilization unit may include a control unit 114. Control unit 114 is relatively simple and comprises primarily a timer switch dial. The dial is turned to a desired time and the UV light is on as long as the timer is counting down. When the timer reaches zero, the UV light turns off. This is similar to the dials discussed above with respect to sterilization chamber 10. This type of timer switch dial may be used with sterilization chamber 10 or the other sterilization units described herein. Optionally, a user interface, control unit, computer, and/or other controls the same as or similar to the user interface, control unit, computer, and other controls discussed above with respect to the sterilization chamber 10 may be used for the sterilization unit 100 or the other sterilization units described herein. The user interface, control unit, computer, etc. used may desirably be capable of controlling the sterilization unit 100 from a remote location, so the user interface, control unit, computer, etc. may be kept away from any MRI equipment when sterilizing an MRI suite. For example, a control unit may have a long cord (e.g., 15-30 feet) and a long distance transformer, so it can be located outside an MRI suite while controlling and powering sterilization unit 100 inside the MRI suite.

Preferably, the entire sterilization unit 100, including its components, is made of aluminum or other non-magnetic materials so that the sterilization unit 100 may be used in the vicinity of an MRI machine without causing problems, as discussed above with respect to sterilization chamber 10. Also, the sterilization unit 100 may be adjustable with respect to its power level. This may be accomplished in ways similar to those discussed above with respect to sterilization chamber 10, e.g., the lights may be interchangeable, only certain lights may be turned on while others are off, light bulbs of different watt levels may be used, etc.

Various methods of using the directed-light UV sterilization unit 100 are possible. Often, the methods of use will involve one or more of the following steps, including moving the sterilization unit 100 over to an item/object (e.g., a chair, equipment, or other furniture) to be sterilized, the base 108 may be rolled under the item/object (e.g., around or between the legs of a chair or desk), the angle and height of the light hood shade 120 may be adjusted to match the item object (e.g., the angle adjustment 104 may be adjusted and/or the height adjustment slide 106 may be adjusted). If wing or extension portions are included, then the wing or extension portions may be swung down to cover the sides of the item/object. Then the sterilization unit 100 may be turned on with the UV light focused primarily on the item/object to be sterilized without exposing any surrounding people to the UV light (or at least minimizing exposure thereto). The sterilization may be done for a desired amount of time sufficient to kill or render non-viable any microorganisms on the item/object. If additional features among those discussed above are used, the method of use may involve using those features as discussed above.

Methods of manufacture may include assembling some or all of the various features described above with respect to the sterilization unit 100.

Figure 8:
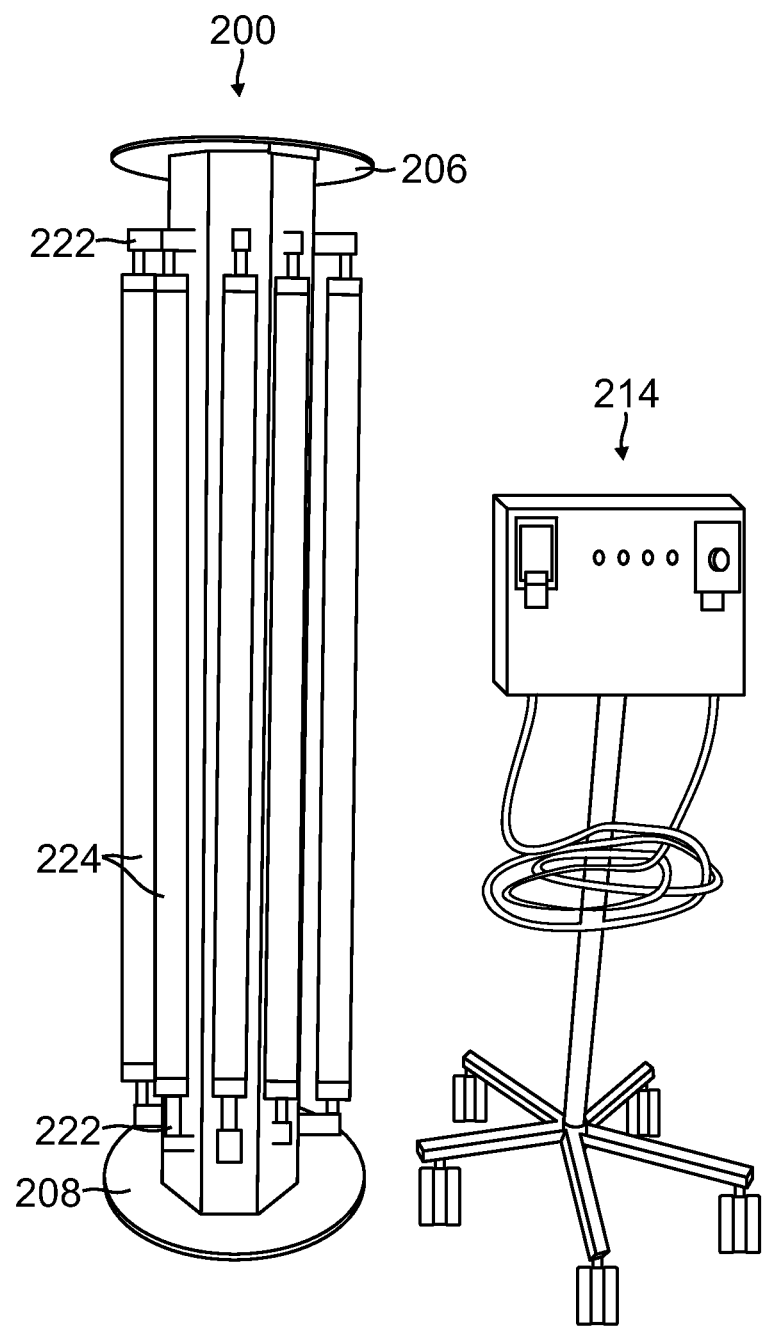
FIG. 8 shows a front view of an exemplary upright tower UV sterilization unit and associated control unit.
Figure 9:
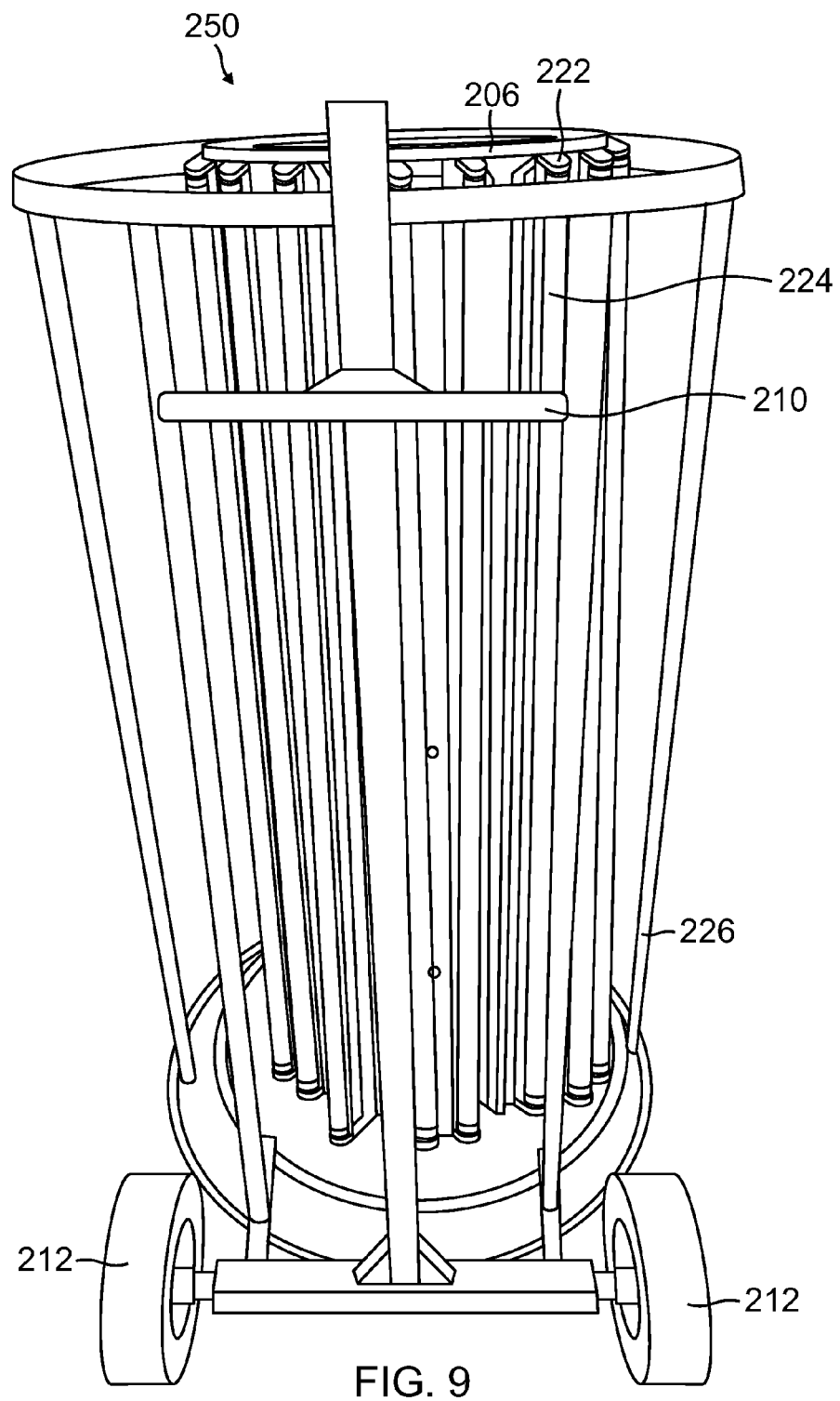
FIG. 9 shows a rear view of an exemplary upright tower UV sterilization unit with exemplary wheels and handle configuration.
Figure 10:
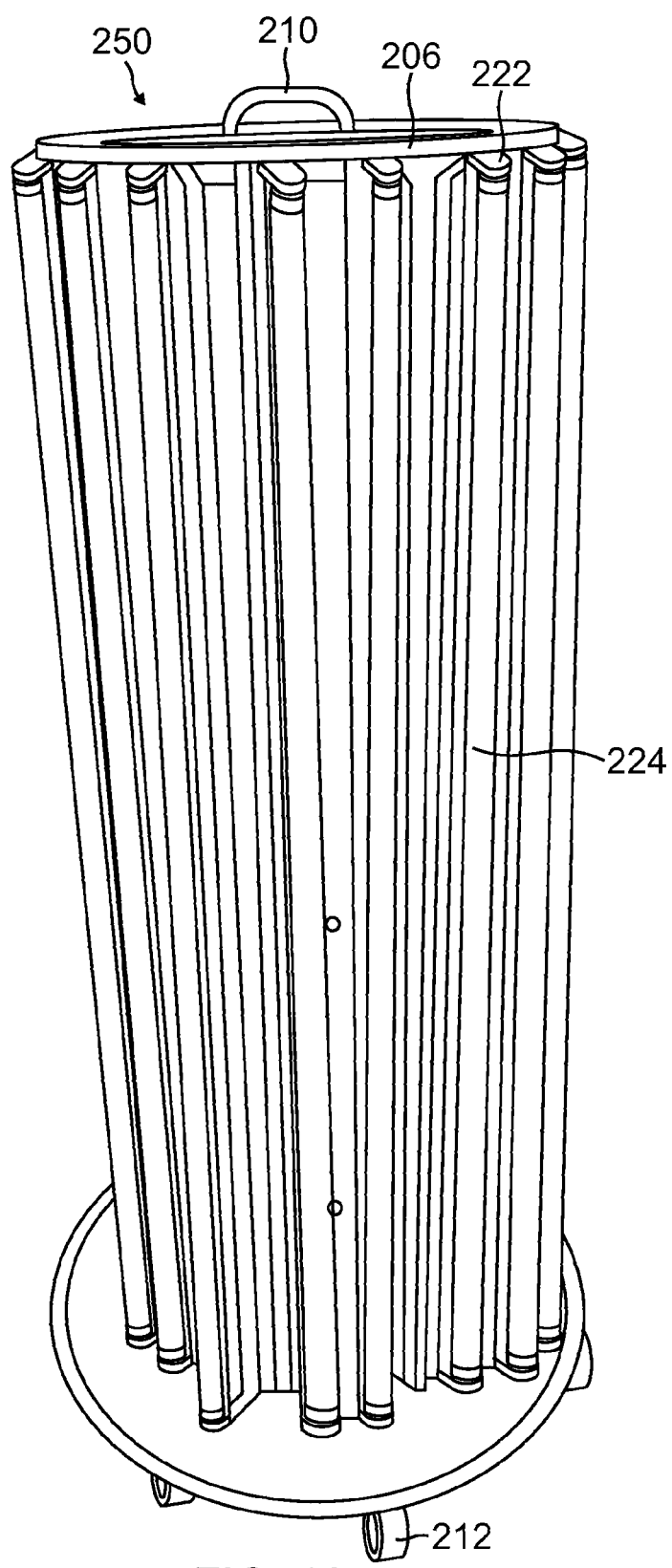
FIG. 10 shows a front view of an exemplary upright tower UV sterilization unit with another configuration of exemplary wheels and handle.

FIG. 8 shows a front view of an exemplary upright tower UV sterilization unit 200 and associated control unit 214. FIG. 9 shows a rear view of an embodiment of the upright tower UV sterilization unit 250. FIG. 10 shows a front view of an embodiment of the upright tower UV sterilization unit 280.

The upright tower UV sterilization unit 200 may be formed as a free standing tower that may be placed in a room to sterilize the room. Preferably, the upright tower UV sterilization unit 200 is formed of aluminum and/or other non-magnetic materials so that the upright tower UV sterilization unit 200 may be used in an MRI room or otherwise in the vicinity of MRI equipment without causing a problem (see discussion above with respect to sterilization chamber 10 and MRI). Even the light fixtures 222 may be made with plastic (including plastic ends) to avoid having magnetic metal material in the unit. However, if the tower unit 200 is not to be used in the vicinity of MRI equipment other metal materials, including those that are magnetic, may be used.

The upright tower UV sterilization unit 200 may be of various shapes and sizes. The upright tower UV sterilization unit 200 is generally made to be tall so that it can effectively flood a room with UV light. Optionally, the upright tower UV sterilization unit 200 is in the range of 20-100 inches or 50-100 inches tall and, optionally, in the range of 40-84 inches or 60-84 inches tall. In one embodiment, the upright tower UV sterilization unit 200 is 72 inches tall. In one embodiment, the upright tower UV sterilization unit 200 is 48 inches tall or 45-55 inches tall. The UV light bulbs 224 may be between 6 inches and 60 inches long, more preferably the UV light bulbs 224 are between 36 inches and 60 inches long. In one embodiment the UV light bulbs 224 are 60 inches long. Alternatively, the UV light bulbs 224 may consist of an array of UV sterilization compact fluorescent lamps (CFL), (similar to an 'energy saver bulb'). A variety of arrangements of the CFL array (e.g. a grid layout, a diamond layout, star-shaped layout, a hexagonal or 'honey comb' lay out) are possible and fall within the scope of the present disclosure.

The upright tower UV sterilization unit 200 may have a variety of cross sectional shapes, including circular, decagonal, nonagonal, octagonal, heptagonal, hexagonal, pentagonal, star-shaped, or square, and UV light bulbs 224 may be arranged on all sides of the unit. The walls of the upright tower UV sterilization unit 200 may be made of a reflective material, e.g., a reflective aluminum, a mirror, or mirror-like material. The reflective material help direct the UV light outwardly to sterilize a room and its contents. Optionally, the reflective material may be corrugated or otherwise patterned as discussed above with respect to the sterilization chamber 10. The base 208 may also be made of a reflective material to help distribute the UV light throughout the room. Also, the upright tower UV sterilization unit 200 may be adjustable with respect to its power level. This may be accomplished in ways similar to those discussed above with respect to sterilization chamber 10, e.g., the lights may be interchangeable, only certain lights may be turned on while others are off, light bulbs of different watt levels may be used, etc.

In FIG. 8, the upright tower UV sterilization unit 200 is shown as being octagonal or having 8 sides. Each of the eight sides has a UV light bulb 224. The UV light bulbs 224 are connected between plastic light fixture ends 222 that are non-magnetic. Light fixtures 222 and UV light bulbs 224 may be the same as or similar to the light fixtures 22 and UV light bulbs 24 discussed above with respect to the sterilization chamber 10. Ultraviolet-transparent protective material similar to that discussed above with respect to the sterilization chamber 10 may be installed over the one or more of the UV light bulbs 224.

The upright tower UV sterilization unit 200 may include a hinge (not shown) along one side and a latching mechanism (e.g., a latch, hitch, clasp, etc.) on the opposite side (not shown); these allow the upright tower UV sterilization unit 200 to be opened and have the interior and any electronics therein serviced. Alternatively, the top piece 206 and/or base 208 could be removed to allow the interior and any electronics therein serviced. The upright tower UV sterilization unit 200 may include wheels on its base 208 or handles or may be otherwise portable, so the unit may be moved from room to room to sterilize different areas.

The control unit 214 may be used to control the upright tower UV sterilization unit 200. As can be seen in FIG. 8, the control unit 214 may include a series of switches, which may be used to adjust power settings and/or control the UV light bulbs (e.g., turn the lights on or off, or turn certain lights on and certain lights off). The control unit 214 may also include a timer switch dial as discussed above with respect to sterilization chamber 10 and sterilization unit 100, which may turn the UV lights on for a set amount of time. A control unit the same as or similar to control unit 214 may be used with sterilization chamber 10 or the other sterilization units described herein. Optionally, a user interface, control unit, computer, and/or other controls the same as or similar to the user interface, control unit, computer, and other controls discussed above with respect to the sterilization chamber 10 may be used for the upright tower UV sterilization unit 200 or the other sterilization units described herein. The user interface, control unit, computer, etc. may desirably be capable of controlling the upright tower UV sterilization unit 200 from a remote location, so the user interface, control unit, computer, etc. may be kept away from any MRI equipment when sterilizing an MRI suite. For example, control unit 214 has a long cord (e.g., 15-30 feet) and a long distance transformer, so it can be located outside an MRI suite while controlling and powering the upright tower UV sterilization unit 200 inside the MRI suite.

FIGS. 9-10 show various embodiments of the upright tower UV sterilization unit 200. The upright tower UV sterilization unit 250 may be formed as a free standing tower that may be placed in a room to sterilize the room. Preferably, the upright tower UV sterilization unit 250 is formed of aluminum and/or other non-magnetic materials as discussed above with respect to the upright tower UV sterilization unit 200. Even the light fixtures 222 may be made with plastic (including plastic ends) to avoid having magnetic metal material in the unit. However, if the tower unit 250 is not to be used in the vicinity of MRI equipment, other metal materials, including those that are magnetic, may be used.

The upright tower UV sterilization unit 250 may be of various shapes and sizes. The upright tower UV sterilization unit 250 illustrates a shorter embodiment of upright tower UV sterilization unit 200. The upright tower UV sterilization unit 250 may be in the range of 20-60 inches tall, but more preferably in the range of 45-55 inches tall. In one embodiment, the upright tower UV sterilization unit 250 is 50 inches tall and uses UV light bulbs 224 that are 48 inches long.

The upright tower UV sterilization unit 250 may have a variety of cross sectional shapes, as discussed above with respect to the upright tower UV sterilization unit 200, and UV light bulbs 224 may be arranged on all sides of the unit. The walls of the upright tower UV sterilization unit 200 may be made of a reflective material, e.g., a reflective aluminum, a reflective Plexiglas, a mirror, or a mirror-like material. The reflective material help direct the UV light outwardly to sterilize a room and its contents. Optionally, the reflective material may be corrugated or otherwise patterned as discussed above with respect to the UV sterilization unit 200. The base 208 may also be made of a reflective material to help distribute the UV light throughout the room. Also, the upright tower UV sterilization unit 250 may be adjustable with respect to its power level. This may be accomplished in ways similar to those discussed above with respect to the UV sterilization unit 200.

In FIGS. 9 and 10, the upright tower UV sterilization unit 250 may be the same as or similar to the UV sterilization unit 200 discussed above, but sized and/or shaped differently. The UV sterilization unit 250 is shown as being octagonal or having 8 sides. Each of the eight sides has a UV light bulb 224. The UV light bulbs 224 are connected between plastic light fixture ends 222 that are non-magnetic. Light fixtures 222 and UV light bulbs 224 may be the same as or similar to the light fixtures 22 and UV light bulbs 24 discussed above with respect to the sterilization chamber 10. Ultraviolet-transparent protective material similar to that discussed above with respect to the sterilization chamber 10 may be installed over the one or more of the UV light bulbs 224.

The upright tower UV sterilization unit 250 may include a hinge (not shown) along one side and a latching mechanism (e.g., a latch, hitch, clasp, etc.) on the opposite side (not shown); these allow the upright tower UV sterilization unit 250 to be opened and have the interior and any electronics therein serviced. Alternatively, the top piece 206 and/or base 208 could be removed to allow the interior and any electronics therein serviced.

FIG. 9 shows one embodiment of the upright tower UV sterilization unit 250 that includes wheels 212 mounted to side of the base 208 and a handle 210 mounted above the wheels, close to the top piece 206 of the unit. When the upright tower UV sterilization unit 250 is resting on its base 208 the wheels 212 may or may not be touching the floor. In order to move the upright tower UV sterilization unit 250, a person would grasp handle 210 and tilt the upright tower UV sterilization unit 250 towards the wheels 212. With the upright tower UV sterilization unit 250 resting on the wheels 212, a person would be able to move the upright tower UV sterilization unit 250 from room to room to sterilize different areas. The UV light bulbs 224 are covered by a protective metal frame 226 that prevents damage to the UV light bulbs and thereby prevent injury to the user from cuts or electrocution associated with broken bulbs.

FIG. 10 shows an embodiment of the upright tower UV sterilization unit 250 that includes wheels 212 mounted to the underside of the base 208 and a handle 210 mounted on the top side of the top piece 206 of the unit. With the upright tower UV sterilization unit 250 resting on the wheels 212, a person would be able to grasp the handle 210 to move the upright tower UV sterilization unit 250 from room to room to sterilize different areas.

Various methods of using the upright tower UV sterilization unit 200 or UV sterilization unit 250 are possible. Often, the methods of use will involve one or more of the following steps, including moving the upright tower UV sterilization unit 200/250 into a room to be sterilized. The upright tower UV sterilization unit 200/250 may be positioned in the room according to the sterilization needs. Then the upright tower UV sterilization unit 200/250 may be turned on exposing the room (preferably the entire room or the portion of the room desired to be sterilized) to the UV light. The sterilization may be done for a desired amount of time sufficient to kill or render non-viable any microorganisms on the item/object. If additional features among those discussed above are used, the method of use may involve using those features as discussed above.

Methods of manufacture may include assembling some or all of the various features described above with respect to the upright tower UV sterilization unit 200 or UV sterilization unit 250.

FIGS. 11-14a each show an exemplary floor-treating, UV sterilization unit 300. Sterilization unit 300 may be used to sterilize various items/objects and rooms. Sterilization unit 300 is particularly useful for sterilizing floors and long narrow regions, e.g., corridors, halls, trailers, etc. Sterilization unit 300 may be constructed with various materials including the materials used to construct the other sterilization units and chamber described herein, e.g., steel, aluminum, plastic, etc. The materials may be reflective of UV light. In one embodiment, the material on the same side of the sterilization unit 300 as the UV light bulbs 324 may be lined with a corrugated or otherwise patterned reflective material similar to that discussed above. In one embodiment, as with the other sterilization units and chamber described herein, it may be desirable to construct the sterilization unit 300 out of non-magnetic materials for the reasons discussed above with respect to the other sterilization units and chamber.

Sterilization unit 300 may be formed of a frame, light fixtures, UV light bulbs, wheels, etc. Sterilization unit 300 may include a central portion 302. The central portion 302 may be a variety of shapes, including generally rectangular or square in shape. The central portion 302 may be formed as part of an open frame of the sterilization unit 300, or the central portion 302 may include a panel attached to a central region of the frame. The central portion 302 may have wheels 308 attached to a bottom or floor-facing side thereof (e.g., four wheels with one at each corner of the central portion 302). The wheels 308 may optionally be attached to legs or extensions 310 extending from the central portion 302 to raise the central portion 302 higher from the floor or ground. In one embodiment, the legs or extensions 310 may be adjustable, so a user may change the distance between the wheels 308 and the central portion 302 to change the height of the central portion 302 above the floor or ground. In one embodiment, the wheels are 10 inches in diameter, but various wheel sizes are possible.

Figure 11:
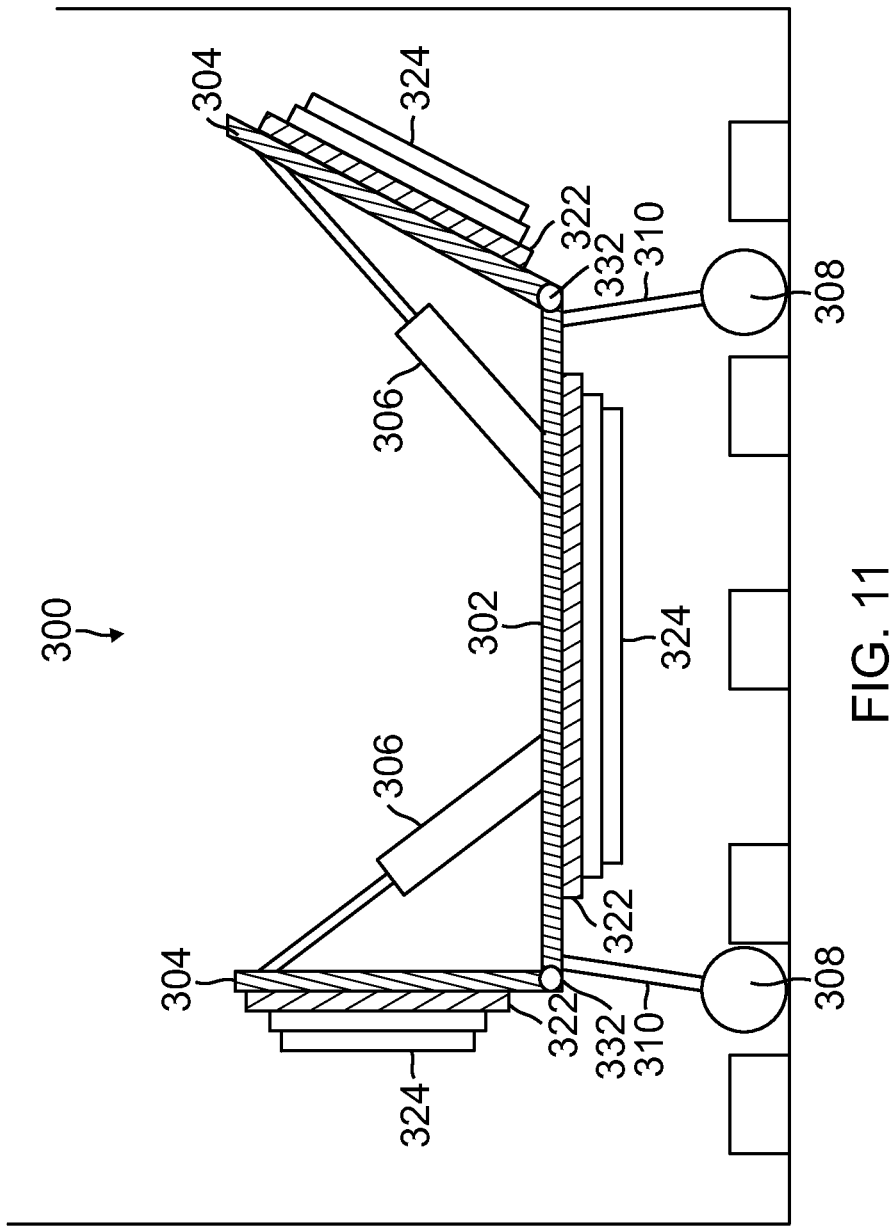
FIG. 11 shows an end view of an exemplary floor-treating, UV sterilization unit.
Figure 12:
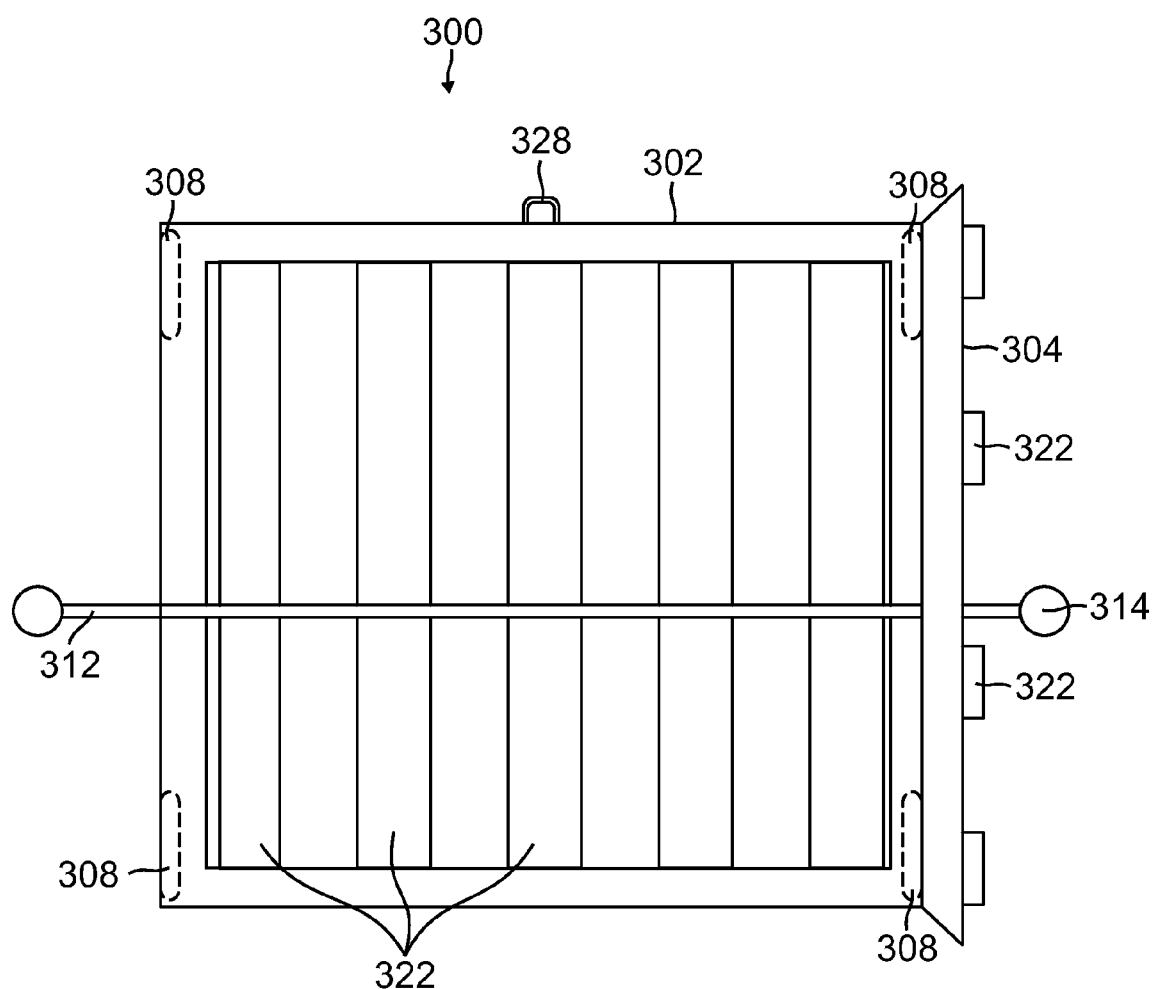
FIG. 12 shows a top view of an exemplary floor-treating, UV sterilization unit of FIG. 11.

The bottom or floor-facing side of the central portion 302 may also include light fixtures 322 and UV light bulbs 324 attached thereto, so that the UV light bulbs 324 shine the UV light downward toward the floor or ground. If the central portion 302 includes an open frame portion, the light fixtures 322 may be attached at either end to the frame, e.g., similar to the embodiment shown in FIG. 12. FIG. 12 shows a top view of a sterilization unit 300 with the UV light bulbs 324 running lengthwise from the front to the back of the sterilization unit 300. The tops of the light fixtures 322 in which the UV light bulbs 324 are installed are visible in FIG. 12 because they span an open area between the sides of the central frame region which allows the tops of the light fixtures 322 to be seen through the open area in the frame. However, the UV light bulbs 324 are on the underside of the light fixtures 322 facing the floor, so they are not visible in FIG. 12. If central portion 302 includes an panel (e.g., an aluminum panel) or other structure closing the frame, then the light fixtures 322 may be attached to a bottom surface thereof, e.g., as shown in FIG. 11. In FIG. 11, the light fixture 322 runs from side to side instead of back to front as in FIG. 12, but either configuration or other configurations of the lights are also possible. Light fixtures 322 and UV light bulbs 324 may be the same as or similar to the light fixtures 22 and UV light bulbs 24 discussed above with respect to the sterilization chamber 10. The UV light bulbs 324 may be between 6 inches and 60 inches long, more preferably the UV light bulbs 324 are between 24 inches and 48 inches long. In one embodiment the UV light bulbs 324 are 48 inches long. Alternatively, the UV light bulbs 324 may consist of an array of UV sterilization compact fluorescent lamps (CFL), (similar to an 'energy saver bulb'). A variety of arrangements of the CFL array (e.g. a grid layout, a diamond layout, a hexagonal or 'honey comb' lay out) are possible and fall within the scope of the present disclosure.

Ultraviolet-transparent protective material similar to that discussed above with respect to the sterilization chamber 10 may be installed over the one or more of the UV light bulbs 324. The material of the central portion 302 may be reflective on the floor facing side as well to help focus and/or direct the light. The wheels 308 (or wheels 308 and legs/extensions 310) are preferably tall enough to keep the UV light bulbs and light fixtures 2-12 inches above the floor or ground. If the legs/extensions 310 are height adjustable, a desired height above the ground may be selected.

Optionally, central portion 302 may include an attachment point 328 (e.g., a hitch, a loop, etc.) at which a cable, line, rope, etc. may be attached to the central portion 302. The cable, line, rope, etc. may be used to pull the sterilization unit 300 across a floor or other area to be sterilized. In one embodiment, a spool or reel may be positioned a distance away (e.g., at an opposite end of a floor or corridor) from the remainder of the sterilization unit 300, and the spool or reel may be used to pull the cable, line, rope, etc. and thereby pull the central portion 302 over the floor/ground to sterilize the floor. The reel or spool or another retraction device may be automated, so a user need not draw the cable, line, rope, etc. directly himself or herself. Generally, each portion of the floor/ground should be exposed to the UV light for at least 3 minutes; however, the exposure may also be longer (e.g., 4 minutes, 5 minutes, etc.). In one embodiment, the sterilization unit uses UV light bulbs that are four feet long and moves at a rate of about one foot per minute to ensure each portion of the floor is exposed to the UV light for four minutes.

Figure 13:
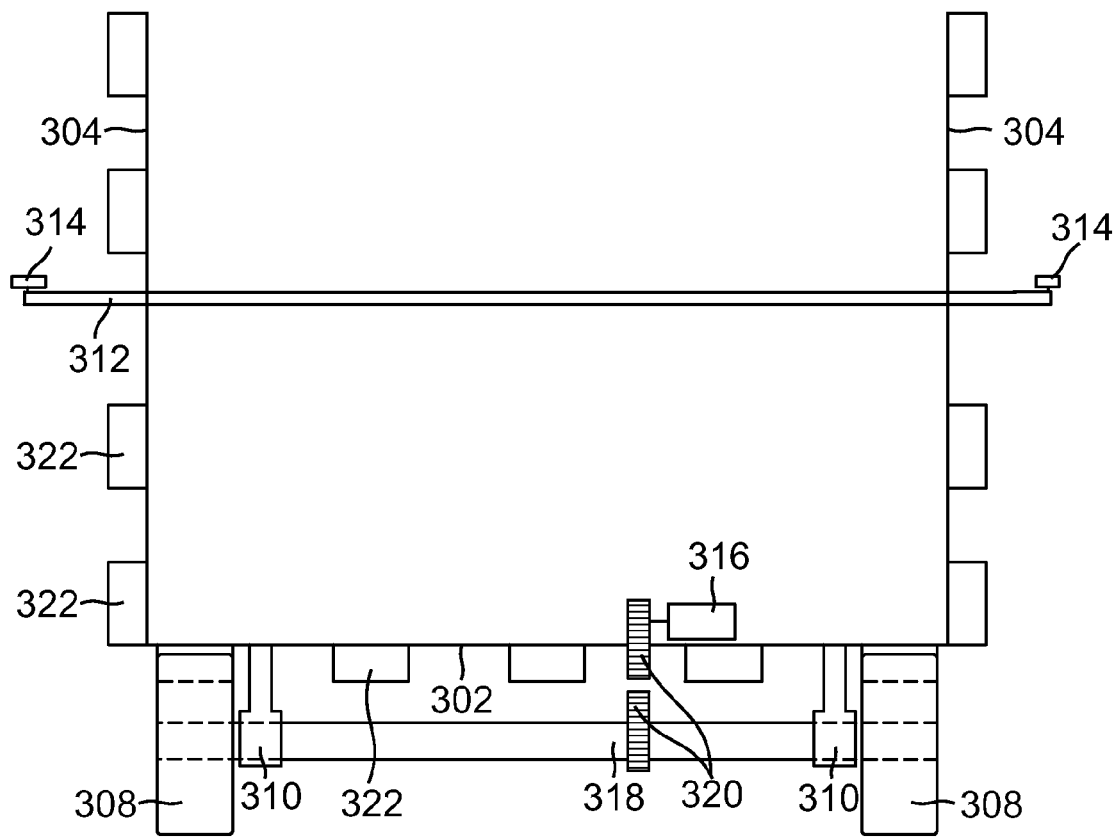
FIG. 13 shows a front view of the exemplary floor-treating UV, sterilization unit of FIG. 11.
Figure 14A:
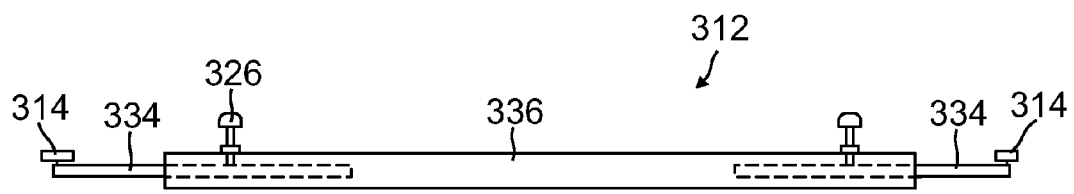
FIG. 14a shows a side view of an exemplary control bar or guide that may be used with the floor-treating UV, sterilization unit of FIG. 14.
Figure 14:
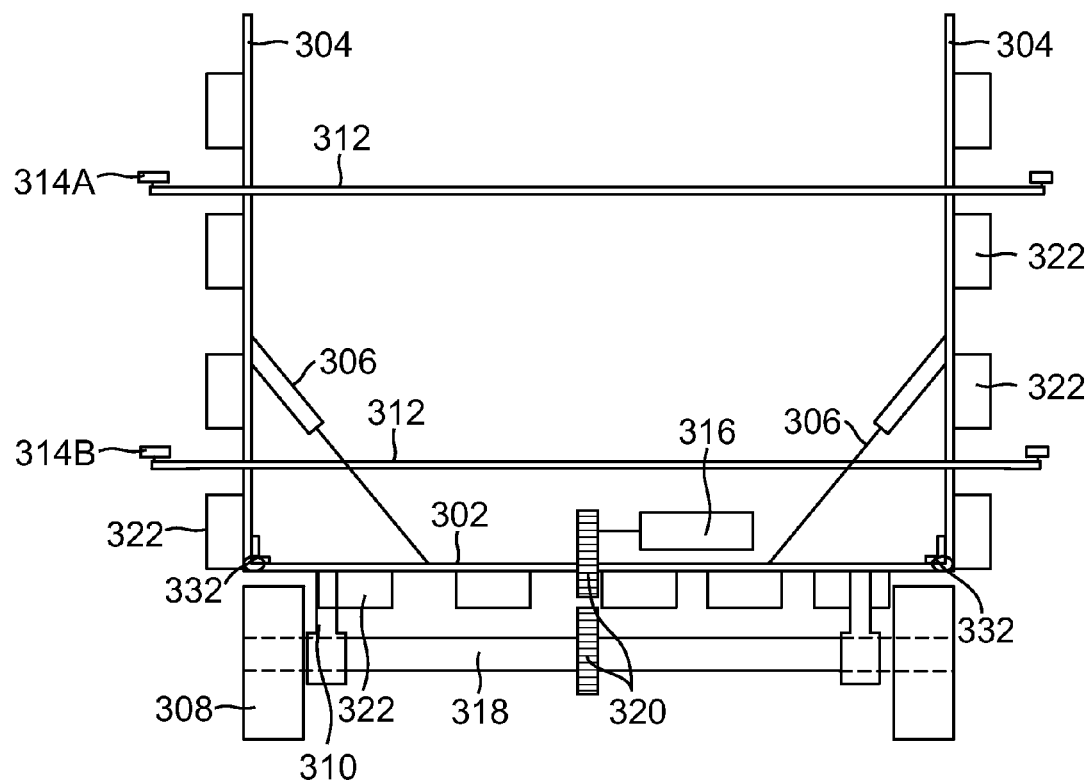
FIG. 14 shows a rear view of an exemplary floor-treating UV, sterilization unit of FIG. 11.

In one embodiment, the sterilization unit 300 may be motorized instead of or in addition to having an attachment point 328 for attaching a line and pulling the unit. The motorized sterilization unit may be able to move the wheels and thereby the sterilization unit without pulling. The motorized sterilization unit may be remote controlled (e.g., similar to a remote controlled car) or programmed (e.g., with software) to drive in a particular pattern or route. In one embodiment, the sterilization unit 300 may include a motor 316 that turns a gear(s) 320 and/or an axle 318 between two wheels. If an axle 318 is used between the wheels, extensions 310 may be axle supports (e.g., as shown in FIGS. 13 and 14) and connect to the axle 318, rather than connecting directly to the wheel 308. In one embodiment, as shown in FIGS. 13-14, two gears 320 are used (although more may be used), e.g., the motor turns a first gear, and the first gear turns a second gear on an axle 318 between two of the wheels 308, and the second gear turns the axle 318 to move the sterilization unit 300. The gears 320 may be in an engaged position or, optionally, they may be in a disengaged position. The two gears 320 of FIGS. 13-14 are shown in a disengaged position for clear differentiation between the gears. Other options beyond gears may be used as well, e.g., a pulley or belt system that transfers motion from the motor to the axle.

The sterilization unit 300 may include one or more control bars or guides 312 to help guide the sterilization unit 300. For example, if the sterilization unit 300 is used in a trailer, corridor, hall, etc., the sterilization unit 300 may include one or more control bars or guides 312 to help keep the sterilization unit 300 from turning off course. The control bar(s) or guides 312 may include wheels 314 (e.g., 3 inch wheels, or other size wheels) on the ends thereof. FIG. 12 shows a top view of wheels 314. FIGS. 13-14 show a side view of wheels 314, which are orientated horizontally to roll along walls as the unit moves. The control bar(s) or guides 312 may be adjustable to change their length, so the wheels 314 may be brought into contact with the walls of a trailer, corridor, hall, etc. FIG. 14a, shows one embodiment of a control bar in which the control bar 312 is constructed of a larger diameter center tube 336, two smaller diameter tubes 334 or bars that are slidable within the larger diameter center tube when not locked, and locks 326 (e.g., tightening screws or lock pins) that can be set to lock or prevent the smaller diameter tubes 334 or bars from sliding in the larger diameter center tube 336. By adjusting the locks/screws 326 and sliding the smaller diameter tubes 334 or bars, the length of the control bar may be adjusted. In use, control bars or guides 312 may be adjusted to fit wheels 314 against the walls of a trailer, corridor, hall, etc. such that the wheels 314 may roll along the walls, but will help prevent the sterilization unit 300 from turning off course. In one embodiment, two control bars 312 may be attached to central portion 302 and/or a frame of the sterilization unit 300. The control bars 312 are preferably spaced apart, e.g., a first control bar 312A near or relatively closer to a first axle between two wheels and a second control bar 312B near or relatively closer to a second axle between two other wheels, to better prevent the sterilization unit 300 from turning off course. The control bars may be placed at the same height off the floor or different heights. In one embodiment, guides are used that extend out from an edge(s) or end(s) of the sterilization unit 300, and do not traverse from side to side across the sterilization unit 300 as control rod 312 does in FIG. 12.

The sterilization unit 300 may include one or more side or wing portions 304 attached to the central portion 302 (e.g., at a side(s) or an end(s) of the central portion 302). The side or wing portions 304 may have a variety of shapes, including generally rectangular or square. The side or wing portions 304 may be formed by an open frame portion of the sterilization unit 300 or have panels or other material covering the frame, e.g., similar to the central portion 302. The side or wing portions 304 may include light fixtures 322 and UV light bulbs 324 on an outer side thereof. The light fixtures 322 and light bulbs 324 may be arranged in various configurations including vertically (FIG. 12) or horizontally (FIGS. 13-14). If the frame of the side or wing portions 304 is open, the light fixtures 322 may be attached directly to the frame and span the open area between edges of the frame. If a panel or other material covers the frame, then the light fixtures 322 may be attached to the panel or other material. The material of the side or wing portions 304 may be reflective on the same side as the UV light bulbs 324 to help focus and/or direct the light. The side or wing portions 304 may be attached to the side edges of the central portion 302, e.g., by hinges 332. The side or wing portions 304 may articulate with respect to the central portion 302, and may include an adjustment mechanism 306 (e.g., extension rod(s); joint(s); latch(es); hydraulic system, and/or a strap(s) and a peg(s), for example, where the strap may have holes that allows the strap to be set on the peg(s) at different lengths which allows different angles of the side or wing portions) that allows the side or wing portions 304 to articulate to and be locked at different angles with respect to the central portion 302.

A user may be able to adjust the side or wing portions 304 to a desired angle for sterilization. For example, in a narrow corridor, the side or wing portions 304 may be set to a 90° angle with respect to the central portion 302 so that the side or wing portions 304 have light bulbs 324 facing the walls and will sterilize the walls as the central portion 302 sterilizes the floor. Optionally, the side or wing portions 304 may be set to an obtuse or acute angle with respect to the central portion 302. The obtuse angle setting may help sterilize a larger floor area or the corners of a corridor. If the side or wing portions 304 are set to 180° with respect to the central portion 302, then the side or wing portions 304 will also have their light bulbs 324 facing the floor; this allows sterilization of a larger floor area than the central portion 302 could accomplish alone. FIG. 11 shows one of the side or wing portions 304 at about a 90° angle and one of the side or wing portions 304 set at an angle that is obtuse as between the central portion 302 and the side or wing portion 304. If the side or wing portions 304 are set to an acute angle with respect to the central portion 302, they may be angled such that their light bulbs 324 are angled at least partially upward (but may be angled mostly upward as well), which may allow for sterilization of walls and/or the ceiling as the sterilization unit 300 is drawn through a room, corridor, hall, trailer, etc. In one embodiment, the articulation of the side or wing portions 304 may be automated and controlled by a control unit, e.g., the user may set the angle of the side or wing portions 304 on a control unit and the side or wing portions 304 will be automated to move to the selected angle. In this embodiment, the angle may be changed as sterilization progresses and while sterilization unit 300 is drawn through a room, corridor, etc. This allows the sterilization and UV light exposure to be changed to match various different portions of the region being sterilized (e.g., room, corridor, trailer, etc.). Also, the sterilization unit 300 may be adjustable with respect to its power level. This may be accomplished in ways similar to those discussed above with respect to sterilization chamber 10, e.g., the lights may be interchangeable, only certain lights may be turned on while others are off, light bulbs of different watt levels may be used, etc.

Sterilization unit 300 may be particularly useful in the trailers of large trucks (e.g., semi-trailer truck and/or food trucks). For example, in many large food trucks, the trailer portion is filled with meat or other food that may drip on the floor of the trailer. Some of these trailers have a floor pattern of parallel ridges and valleys, which can complicate other forms of cleaning or sterilization. Indeed, FIG. 11 shows an end view of sterilization unit 300 inside of a trailer in which the floor includes parallel ridges and valleys. Food drippings or other contaminants may accumulate on the floor of the trailer. Even when hosed off, the trailer may still include harmful microorganisms. It is desirable to sterilize the trailer before a new shipment of food is taken in the trailer to avoid spreading any contamination or microorganisms. Sterilization unit 300 may be used to effectively sterilize the trailer. For example, the sterilization unit 300 may be placed at the back of the trailer (i.e., furthest from the door, or closest to the cab of the truck). The cable, line, rope, etc. may be attached to the sterilization unit 300 (e.g., at a loop or hitch on the central portion 302), and the cable, line, rope, etc. may be pulled from outside the trailer or at the other end of the trailer to move the sterilization unit 300 along the floor of the trailer. As discussed above, the UV light should be allowed to radiate on each portion of the trailer floor and/or trailer for at least 3 minutes or longer (e.g., 4, 5, or 6 minutes). If side or wing portions 304 are included on the sterilization unit 300, the side or wing portions 304 may be positioned/set at the desired angle for sterilizing the trailer (see discussion of angles of the side or wing portions 304 above). In this way, the trailer floor and/or trailer may be sterilized in one pass from end to end.

The sterilization unit 300 may be controlled by a user interface, control unit, computer, dials, switches, buttons, etc. in the same way or a similar way as discussed above with respect to the sterilization chamber 10, sterilization unit 100, and/or sterilization unit 200. The user interface, control unit, computer, dials, switches, buttons, etc. used with sterilization unit 300 may be the same or similar to the user interface, control unit, computer, dials, switches, buttons, etc. used with the sterilization chamber 10, sterilization unit 100, and/or sterilization unit 200 as discussed above.

Various methods of using the sterilization unit 300 are possible. Often, the methods of use will involve one or more of the following steps, including positioning the sterilization unit 300 in a region of a floor to be sterilized (e.g., at one end of a floor of a room to be sterilized); attaching a line 330 (e.g., a cable or rope) to the sterilization unit 300; turning on the UV lights to irradiate the target area (e.g., an area of the floor) (a control unit or user interface as described herein may be used). Each area treated for sterilization may be exposed to the UV light for a desired amount of time sufficient to kill or render non-viable any microorganisms on the item/object. The line 330 may be pulled or reeled in thereby pulling and moving the sterilization unit through the area to be sterilized and exposing the area to the UV light. If additional features among those discussed above are used, the method of use may involve using those features as discussed above. For example, if the sterilization unit includes side or wing portions 304, the side or wing portions 304 may be adjusted to a desired angle for sterilization of the target area.

Methods of manufacture may include assembling some or all of the various features described above with respect to the UV sterilization unit 300.

Figure 15:
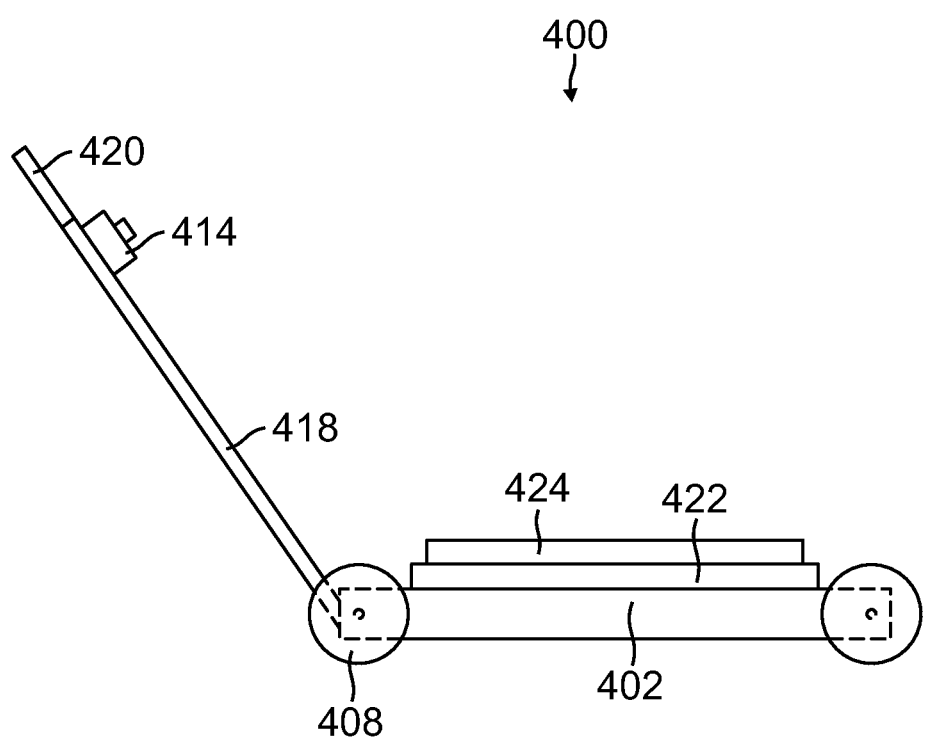
FIG. 15 shows an exemplary under-side UV sterilization unit 400.

FIG. 15 shows an exemplary under-side, UV sterilization unit 400. Sterilization unit 400 may be used to sterilize various items/objects in situ. Sterilization unit 400 is particularly useful for sterilizing the underside of large items/objects that are not easily or impossible to move, e.g., large beds, chairs, tables, cabinets etc. Sterilization unit 400 may be constructed with various materials including the materials used to construct the other sterilization units and chamber described herein, e.g., steel, aluminum, plastic, etc. The materials may be reflective of UV light. In one embodiment, the material on the same side of the sterilization unit 400 as the UV light bulbs 424 may be lined with a corrugated or otherwise patterned reflective material similar to that discussed above. In one embodiment, as with the other sterilization units and chamber described herein, it may be desirable to construct the sterilization unit 400 out of non-magnetic materials for the reasons discussed above with respect to the other sterilization units and chamber.

Sterilization unit 400 may be formed of a frame, light fixtures 422, UV light bulbs 424, wheels 408, and a handle 418. Sterilization unit 400 may include a central portion 402. The central portion 402 may be a variety of shapes, including generally rectangular or square in shape. The central portion 402 may be formed as part of an open frame of the sterilization unit 400, or the central portion 402 may include a panel attached to a central region of the frame. The central portion 402 may have wheels 408 attached to a side of the central portion 402 thereof (e.g., four wheels with one at each corner of the central portion 402). The wheels 408 may optionally be attached to legs or extensions (not shown) extending from the central portion 402 to raise the central portion 302 higher from the floor or ground. In one embodiment, the legs or extensions may be adjustable, so a user may change the distance between the wheels 408 and the central portion 402. In one embodiment, the wheels are 2 inches in diameter, but various wheel sizes are possible.

The top or upward-facing side of the central portion 402 may also include light fixtures 422 and UV light bulbs 424 attached thereto, so that the UV light bulbs 424 shine the UV light upward toward the underside of the item or object being treated. If the central portion 402 includes an open frame portion, the light fixtures 422 may be attached at either end to the frame, e.g., similar to the embodiment shown in FIG. 12. If central portion 402 includes an panel (e.g., an aluminum panel) or other structure closing the frame, then the light fixtures 422 may be attached to a top surface thereof, e.g., as shown in FIG. 15. In FIG. 11, the light fixture 322 runs from front to back, however, other configurations of the lights are also possible e.g. from side to side. Light fixtures 422 and UV light bulbs 424 may be the same as or similar to the light fixtures 22 and UV light bulbs 24 discussed above with respect to the sterilization chamber 10. The UV light bulbs 424 may be between 6 inches and 48 inches long, optionally the UV light bulbs 324 are between 12 inches and 36 inches long. In one embodiment the UV light bulbs 324 are 18 inches long. Alternatively, the UV light bulbs 424 may consist of an array of UV sterilization compact fluorescent lamps (CFL), (similar to an 'energy saver bulb'). It will be obvious to a person of ordinary skill in the art that a variety of arrangements of the CFL array (e.g. a grid layout, a diamond layout, a hexagonal or 'honey comb' lay out, or other layouts described elsewhere herein) are possible and fall within the scope of the present disclosure.

Ultraviolet-transparent protective material similar to that discussed above with respect to the sterilization chamber 10 may be installed over the one or more of the UV light bulbs 424. The material of the central portion 402 may be reflective on the upward facing side as well to help focus and/or direct the light. The wheels 408 (or wheels 408 and legs/extensions) are preferably tall enough to keep the UV light bulbs and light fixtures 2-24 inches above the floor or ground. If the legs/extensions are height adjustable, a desired height above the ground may be selected. The wheels may also be able to extend or telescope relative to each other such that the wheels can be changed between configurations in which the wheels are closer together and configurations in which the wheels are further apart, e.g., the axle between two wheels may be able to telescope to extend and/or retract the wheels toward or away from each other.

Optionally, central portion 402 may include an attachment point at which a handle or pole, etc. may be attached to the central portion 402. The handle or pole etc. may be used to maneuver the sterilization unit 400 underneath an item/object or other area to be sterilized. Generally, each portion of the underside of the item or object to be sterilized should be exposed to the UV light for at least 3 minutes; however, the exposure may also be longer (e.g., 4 minutes, 5 minutes, etc.). At the opposite end of the handle 418 there may be a hand grip 420 to allow a person to comfortably grasp the handle 418 and position the sterilization unit 400. The sterilization unit 400 may also include a shield or reflective barrier between the UV lights and the end user to block or limit UV light from reaching the operator. The handle or pole, etc. may be able to adjust or telescope to change the length of the handle used in different situations.

The sterilization unit 400 may be controlled by a user interface, control unit, computer, dials, switches, buttons, etc. in the same way or a similar way as discussed above with respect to the sterilization chamber 10, sterilization unit 100, and/or sterilization unit 200. The user interface, control unit, computer, dials, switches, buttons, etc. 414 may be positioned close to or on the hand grip 420. The user interface, control unit, computer, dials, switches, buttons, etc. used with sterilization unit 400 may be the same or similar to the user interface, control unit, computer, dials, switches, buttons, etc. used with the sterilization chamber 10, sterilization unit 100, and/or sterilization unit 200 as discussed above.

Various methods of using the sterilization unit 400 are possible. Often, the methods of use will involve one or more of the following steps, including positioning the sterilization unit 400 in a region underneath an item to be sterilized (e.g., underneath a bed); turning on the UV lights to irradiate the target area (e.g., a region underneath an item to be sterilized) (a control unit or user interface as described herein may be used). Each area treated for sterilization may be exposed to the UV light for a desired amount of time sufficient to kill or render non-viable any microorganisms on the item/object. The handle 418 may be used to move the sterilization unit 400 to another area to be sterilized and exposing the area to the UV light.

Methods of manufacture may include assembling some or all of the various features described above with respect to the UV sterilization unit 400.

The above sterilization chambers, units, systems, assemblies, methods, etc. have generally been described as being applied to sterilization of particular types of equipment, furniture, objects/items, rooms, trailers, etc.; however, the principles described may be applied to other types of equipment, furniture, objects/items, rooms, trailers, systems, instruments, etc. Further, features described in one embodiment above, including embodiments described in the Summary section, may generally be combined with features described in other embodiments herein.

Components of the chamber, units, control units, user interfaces, devices, apparatuses, systems, methods, etc. described herein may be implemented in hardware, software, or a combination of both. Where components of the chamber, units, control units, user interfaces, devices, apparatuses, systems, methods, etc. are implemented in software, the software may be stored in an executable format on one or more non-transitory machine-readable mediums. Further, the software and related steps of the methods described above may be implemented in software as a set of data and instructions. A machine-readable medium includes any mechanism that provides (e.g., stores and/or transports) information in a form readable by a machine (e.g., a computer). For example, a machine-readable medium includes read only memory (ROM); random access memory (RAM); magnetic disk storage media; optical storage media; flash memory devices; DVD's, electrical, optical, acoustical or other form of propagated signals (e.g., carrier waves, infrared signals, digital signals, EPROMs, EEPROMs, FLASH, magnetic or optical cards, or any type of media suitable for storing electronic instructions. Information representing the units, systems, and/or methods stored on the machine-readable medium may be used in the process of creating the units, systems, and/or methods described herein. Hardware used to implement the invention may include integrated circuits, microprocessors, FPGAs, digital signal controllers, stream processors, and/or other components.

While the invention has been described in terms of particular variations and illustrative figures, those of ordinary skill in the art will recognize that the invention is not limited to the variations or figures described. The features described with respect to one embodiment or variation may be used in other embodiments or variations. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A sterilization chamber, comprising:
    walls enclosing a sterilization area, including a door forming one wall of the walls enclosing the sterilization area, the door configured to open and close;
    one or more ultraviolet light bulbs attached to one or more of the walls inside the sterilization area, wherein the one or more ultraviolet light bulbs are capable of irradiating germicidal ultraviolet light at sufficient levels to kill or render non-viable microorganisms exposed to the ultraviolet light;
    a corrugated reflective material that lines an inside surface of the walls; and
    a control unit including controls to operate the one or more ultraviolet light bulbs.

2. The sterilization chamber according to claim 1, wherein a side of the door facing the interior of the sterilization chamber when the door is closed includes one of the one or more ultraviolet light bulbs attached thereto.

3. The sterilization chamber according to claim 1, wherein the one or more ultraviolet light bulbs are attached to the one or more of the walls through light fixtures mounted directly to the one or more of the walls.

4. The sterilization chamber according to claim 1, wherein one of the walls includes a window capable of blocking at least 95% of the ultraviolet light from the one or more ultraviolet light bulbs while allowing a user to view the sterilization area during use.

5. The sterilization chamber according to claim 4, wherein the window includes a door or shutter that can close over the window.

6. The sterilization chamber according to claim 1, wherein the lining of corrugated reflective material is configured to reflect the ultraviolet light in the chamber in many different directions to help spread the ultraviolet light on every surface of an object being sterilized in the sterilization area.

7. The sterilization chamber according to claim 1, wherein the walls are constructed of an outer wall layer that forms an outside surface of the sterilization chamber, and an inner wall layer including an opening through which the one or more ultraviolet light bulbs extend.

8. The sterilization chamber according to claim 7, wherein the inner wall layer is positioned such that the one or more ultraviolet light bulbs extend further into the sterilization area than the inner wall layer, but any cords and a majority of any light fixture are between the inner wall layer and the outer wall layer.

9. The sterilization chamber according to claim 8, wherein the corrugated reflective material is integral with the inner wall layer.

10. The sterilization chamber according to claim 1, wherein an ultraviolet-transparent protective material is installed over the one or more ultraviolet light bulbs, the protective material configured to prevent damage to the one or more ultraviolet light bulbs.

11. The sterilization chamber according to claim 10, wherein the ultraviolet-transparent protective material is placed as an inner wall layer and entirely covers one or more of the walls inside the sterilization area.

12. The sterilization chamber according to claim 10, wherein the ultraviolet-transparent protective material is placed as a casing sized to fit around only one of the one or more ultraviolet light bulbs.

13. The sterilization chamber according to claim 1, wherein an ultraviolet-transparent protective material is installed over one or more ultraviolet light bulbs installed on a floor of the sterilization chamber, the protective material extending over an entire surface of the floor and configured to prevent damage to the one or more ultraviolet light bulbs installed on the floor and configured to support objects placed in the sterilization area for sterilization.

14. The sterilization chamber according to claim 1, wherein the one or more ultraviolet light bulbs are adjustable in the sterilization chamber, such that a user may adjust a position of the one or more ultraviolet light bulbs into a desired position.

15. The sterilization chamber according to claim 1, wherein a power level of the ultraviolet light radiating from the one or more ultraviolet light bulbs into the sterilization area is adjustable.

16. The sterilization chamber according to claim 1, wherein the control unit includes a processor, memory, and software, wherein the software allows a user to adjust a power level of ultraviolet light in the sterilization area and adjust a time for sterilization.

17. The sterilization chamber according to claim 1, wherein the door can open wide enough to allow a hospital gurney to enter the sterilization area.

18. The sterilization chamber according to claim 1, wherein the door has a width and a height that are the same as a width and height of the sterilization chamber.

19. The sterilization chamber according to claim 1, wherein a floor of the sterilization chamber has a smooth, reflective surface facing the sterilization area.

20. A method of sterilization comprising:
placing one or more items to be sterilized inside an interior of a sterilization chamber,
the sterilization chamber comprising
walls enclosing a sterilization area, including a door forming one wall of the walls enclosing the sterilization area, the door configured to open and close;
one or more ultraviolet light bulbs attached to one or more of the walls inside the sterilization area, wherein the one or more ultraviolet light bulbs are capable of irradiating germicidal ultraviolet light at sufficient levels to kill or render non-viable microorganisms exposed to the ultraviolet light; and
a corrugated reflective material that lines an inside surface of the walls; and
sterilizing the one or more items by turning on the one or more ultraviolet light bulbs inside the sterilization chamber and leaving them on for an amount of time sufficient to kill or render non-viable 100% or nearly 100% of the microorganisms on the one or more items, wherein ultraviolet light from the one or more ultraviolet light bulbs is reflected in many different directions by the corrugated reflective material such that non-uniform surfaces of the one or more items are exposed to the ultraviolet light.

21. The method according to claim 20, wherein a position of the ultraviolet light bulbs in the sterilization chamber is adjustable, the method further comprising moving the ultraviolet light bulbs in the sterilization chamber to a desired location for sterilization.

22. A sterilization apparatus, comprising:
a base;
a central tower portion attached to the base, wherein the central tower portion has multiple sides of equal size, wherein each of the multiple sides is constructed of a reflective material;
multiple ultraviolet light bulbs, each of the multiple ultraviolet light bulbs attached to a different side of the multiple sides, wherein the multiple ultraviolet light bulbs are capable of irradiating germicidal ultraviolet light at sufficient levels to kill or render non-viable microorganisms exposed to the ultraviolet light; and
a control unit to operate the one or more ultraviolet light bulbs.

23. The sterilization apparatus according to claim 22, wherein each of the base, the central tower portion, and the multiple ultraviolet light bulbs is constructed only of materials that are non-magnetic.

24. The sterilization apparatus according to claim 23, wherein the central tower portion includes a hinge along a first side and a latching mechanism on an opposite, second side, such that the central tower portion may be opened to service an interior of the central tower portion.

25. A method of sterilization comprising:
moving a sterilization device into a room to be sterilized, the sterilization device comprising:
a base;
a central tower portion attached to the base, wherein the central tower portion has multiple sides of equal size, wherein each of the multiple sides is constructed of a reflective material;
multiple ultraviolet light bulbs, each of the multiple ultraviolet light bulbs attached to a different side of the multiple sides, wherein the multiple ultraviolet light bulbs are capable of irradiating germicidal ultraviolet light at sufficient levels to kill or render non-viable microorganisms exposed to the ultraviolet light; and
sterilizing the room to be sterilized by turning on the one or more ultraviolet light bulbs and letting ultraviolet light radiate throughout the room to be sterilized.

26. The method according to claim 25, wherein the sterilizing step is done for an amount of time sufficient to kill or render non-viable any microorganisms on the one or more objects within the room.

* * * * *